US010182874B2

(12) United States Patent
Hasegawa et al.

(10) Patent No.: US 10,182,874 B2
(45) Date of Patent: Jan. 22, 2019

(54) MANIPULATOR SYSTEM INITIALIZATION METHOD

(71) Applicant: OLYMPUS CORPORATION, Tokyo (JP)

(72) Inventors: Mitsuaki Hasegawa, Tokyo (JP); Toshihiro Yoshii, Tokyo (JP)

(73) Assignee: OLYMPUS CORPORATION, Tokyo (JP)

(*) Notice: Subject to any disclaimer, the term of this patent is extended or adjusted under 35 U.S.C. 154(b) by 179 days.

(21) Appl. No.: 15/236,513

(22) Filed: Aug. 15, 2016

(65) Prior Publication Data
US 2016/0374772 A1 Dec. 29, 2016

Related U.S. Application Data

(63) Continuation of application No. PCT/JP2015/054763, filed on Feb. 20, 2015.

(30) Foreign Application Priority Data

Feb. 21, 2014 (JP) .................................. 2014-032247

(51) Int. Cl.
G05B 19/04 (2006.01)
G05B 19/18 (2006.01)
(Continued)

(52) U.S. Cl.
CPC ............... A61B 34/37 (2016.02); A61B 1/00 (2013.01); A61B 34/20 (2016.02); A61B 34/30 (2016.02);
(Continued)

(58) Field of Classification Search
CPC ... A61B 1/00133; A61B 1/0051; A61B 1/018; A61B 18/1442; A61B 18/1492;
(Continued)

(56) References Cited

U.S. PATENT DOCUMENTS 5,496,347 A * 3/1996 Hashiguchi ............ A61B 17/29
600/564
6,234,717 B1 * 5/2001 Corbetta ................. E21B 41/04
405/158
(Continued)

FOREIGN PATENT DOCUMENTS

EP 2 881 061 A1 6/2015
JP H10-174686 A 6/1998
(Continued)

OTHER PUBLICATIONS

Extended Supplementary European Search Report dated Sep. 20, 2017 in European Patent Application No. 15 75 2065.1.
(Continued)

Primary Examiner — Khoi H Tran
Assistant Examiner — Jorge O Peche
(74) Attorney, Agent, or Firm — Scully, Scott, Murphy & Presser, P.C.

(57) ABSTRACT

A manipulator system initialization method includes: a joint angle setting step of bringing a driving force relay part into a driving force release state, inserting a bending joint and a pair of shaft-shaped parts coupled by the bending joint into a shape defining member having a shape defining part that brings a joint angle of the bending joint to a predetermined value, and setting a joint angle of the bending joint to the predetermined value; a drive part coupling step of switching the driving force relay part to a driving force relay state, with respect to the bending joint of which the joint angle is set; and an origin setting step of associating a state of the joint angle of the bending joint with a drive origin of a drive part after the drive part coupling step is performed.

13 Claims, 26 Drawing Sheets

(51) Int. Cl.
  *A61B 34/37* (2016.01)
  *A61B 1/00* (2006.01)
  *B25J 9/16* (2006.01)
  *A61B 34/00* (2016.01)
  *A61B 34/30* (2016.01)
  *A61B 34/20* (2016.01)
  *A61B 17/00* (2006.01)

(52) U.S. Cl.
  CPC ............ *A61B 34/71* (2016.02); *B25J 9/1689* (2013.01); *A61B 2017/00314* (2013.01); *A61B 2017/00327* (2013.01); *A61B 2034/301* (2016.02); *A61B 2034/306* (2016.02)

(58) Field of Classification Search
  CPC . A61B 1/00098; A61B 1/0016; A61B 1/0052; A61B 1/0057; A61B 1/012; A61B 2017/2908; A61B 2090/0811; A61B 34/70; A61B 34/71
  See application file for complete search history.

(56) References Cited

U.S. PATENT DOCUMENTS

| | | | |
|---|---|---|---|
| 6,723,106 B1* | 4/2004 | Charles | B25J 9/1065 606/130 |
| 9,265,405 B2* | 2/2016 | Okamoto | A61B 1/00002 |
| 9,895,813 B2* | 2/2018 | Blumenkranz | B25J 13/085 |
| 2004/0092912 A1* | 5/2004 | Jinno | A61B 17/00234 606/1 |
| 2005/0075538 A1* | 4/2005 | Banik | A61B 1/00071 600/141 |
| 2005/0119527 A1* | 6/2005 | Banik | A61B 1/00059 600/117 |
| 2005/0154262 A1* | 7/2005 | Banik | A61B 1/00059 600/179 |
| 2005/0197536 A1* | 9/2005 | Banik | A61B 1/00059 600/179 |
| 2005/0222499 A1* | 10/2005 | Banik | A61B 1/00059 600/132 |
| 2005/0228224 A1* | 10/2005 | Okada | A61B 1/00071 600/104 |
| 2005/0245789 A1* | 11/2005 | Smith | A61B 1/00059 600/159 |
| 2006/0064113 A1* | 3/2006 | Nakao | A61B 10/06 606/113 |
| 2007/0151390 A1* | 7/2007 | Blumenkranz | A61B 19/2203 74/490.06 |
| 2008/0058861 A1* | 3/2008 | Cooper | A61B 34/70 606/205 |
| 2008/0065111 A1* | 3/2008 | Blumenkranz | B25J 15/0009 606/130 |
| 2008/0103491 A1* | 5/2008 | Omori | A61B 17/29 606/1 |
| 2008/0221592 A1* | 9/2008 | Kawai | A61B 1/0055 606/130 |
| 2009/0012365 A1* | 1/2009 | Ueno | A61B 1/0052 600/146 |
| 2009/0105726 A1* | 4/2009 | Sugiyama | A61B 18/1492 606/130 |
| 2009/0112060 A1* | 4/2009 | Sugiyama | A61B 1/00098 600/104 |
| 2009/0248038 A1* | 10/2009 | Blumenkranz | B25J 13/085 606/130 |
| 2009/0253959 A1* | 10/2009 | Yoshie | A61B 1/00133 600/114 |
| 2009/0326318 A1* | 12/2009 | Tognaccini | A61B 1/00183 600/104 |
| 2010/0030023 A1* | 2/2010 | Yoshie | A61B 1/00147 600/117 |
| 2010/0082041 A1* | 4/2010 | Prisco | B25J 9/1045 606/130 |
| 2010/0106167 A1* | 4/2010 | Boulnois | A61B 17/1285 606/142 |
| 2010/0160728 A1* | 6/2010 | Yoshie | A61B 1/00147 600/109 |
| 2011/0184234 A1* | 7/2011 | Morgenstren Lopez | A61B 5/417 600/107 |
| 2011/0277775 A1* | 11/2011 | Holop | A61B 17/3423 128/849 |
| 2012/0172667 A1* | 7/2012 | Takeuchi | A61B 1/0052 600/140 |
| 2012/0259319 A1* | 10/2012 | Stefan | A61B 17/29 606/1 |
| 2015/0005580 A1* | 1/2015 | Petersen | A61B 1/0008 600/112 |
| 2015/0045812 A1* | 2/2015 | Seo | A61B 34/30 606/130 |
| 2015/0148607 A1* | 5/2015 | Naito | A61B 1/00154 600/114 |
| 2016/0001038 A1* | 1/2016 | Romo | A61M 25/005 604/526 |
| 2016/0184032 A1* | 6/2016 | Romo | A61B 10/04 606/130 |
| 2016/0206337 A1* | 7/2016 | Karcher | A61B 17/29 |
| 2017/0065364 A1* | 3/2017 | Schuh | A61B 34/70 |
| 2017/0156817 A1* | 6/2017 | Singh | A61B 90/10 |
| 2017/0333143 A1* | 11/2017 | Yoshii | A61B 1/00 |
| 2017/0340396 A1* | 11/2017 | Romo | A61B 10/04 |
| 2017/0347863 A1* | 12/2017 | Takahashi | A61B 17/28 |
| 2018/0014852 A1* | 1/2018 | Gomez | A61B 17/3423 |

FOREIGN PATENT DOCUMENTS

| | | |
|---|---|---|
| JP | 2006-149878 A | 6/2006 |
| JP | 2007-029167 A | 2/2007 |
| JP | 2008-104854 A | 5/2008 |
| JP | 2009-100873 A | 5/2009 |
| JP | 2009-101077 A | 5/2009 |
| JP | 2009-247619 A | 10/2009 |
| JP | 2012-504016 A | 2/2012 |
| JP | 2013-094452 A | 5/2013 |
| JP | 2013-519431 A | 5/2013 |
| WO | WO 2010/039387 A1 | 4/2010 |
| WO | WO 2011/100110 A1 | 8/2011 |
| WO | WO 2013/065859 A1 | 5/2013 |
| WO | 2014/021122 A1 | 2/2014 |

OTHER PUBLICATIONS

Japanese Office Action dated Jun. 6, 2017 in Japanese Patent Application No. 2014-032247.
International Search Report dated May 26, 2015 issued in PCT/JP2015/054763.

* cited by examiner

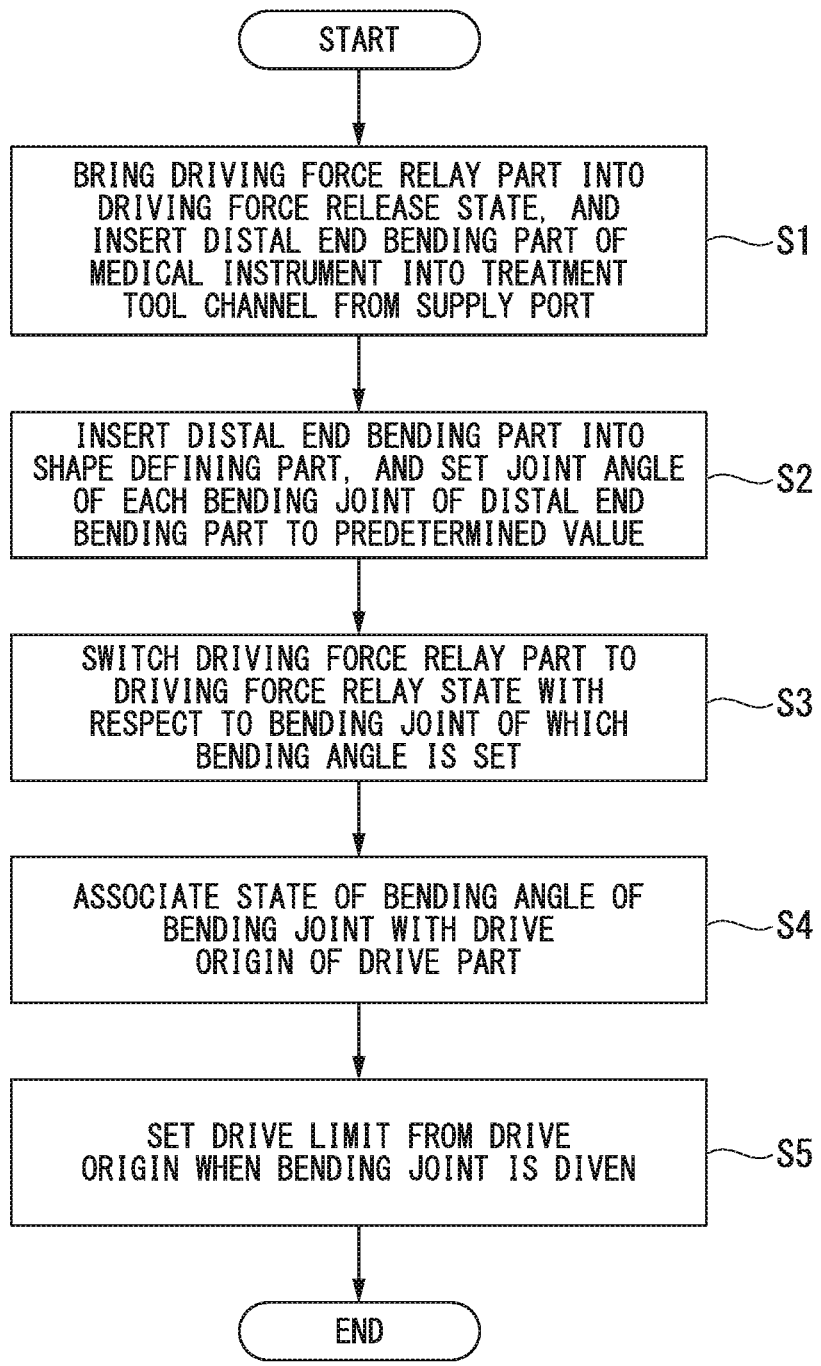

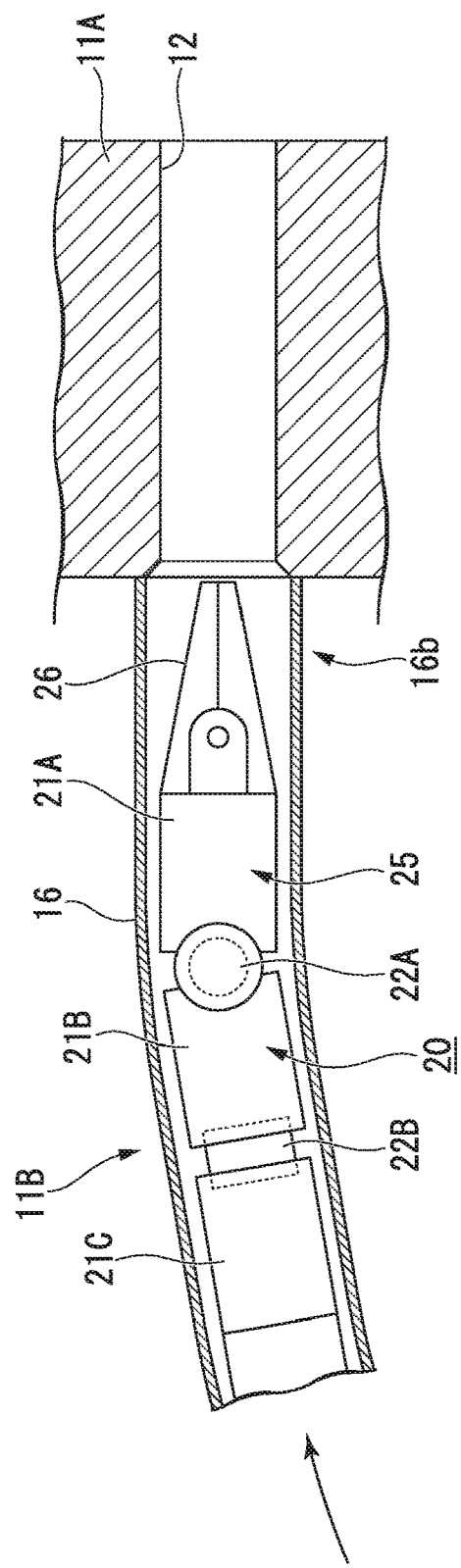

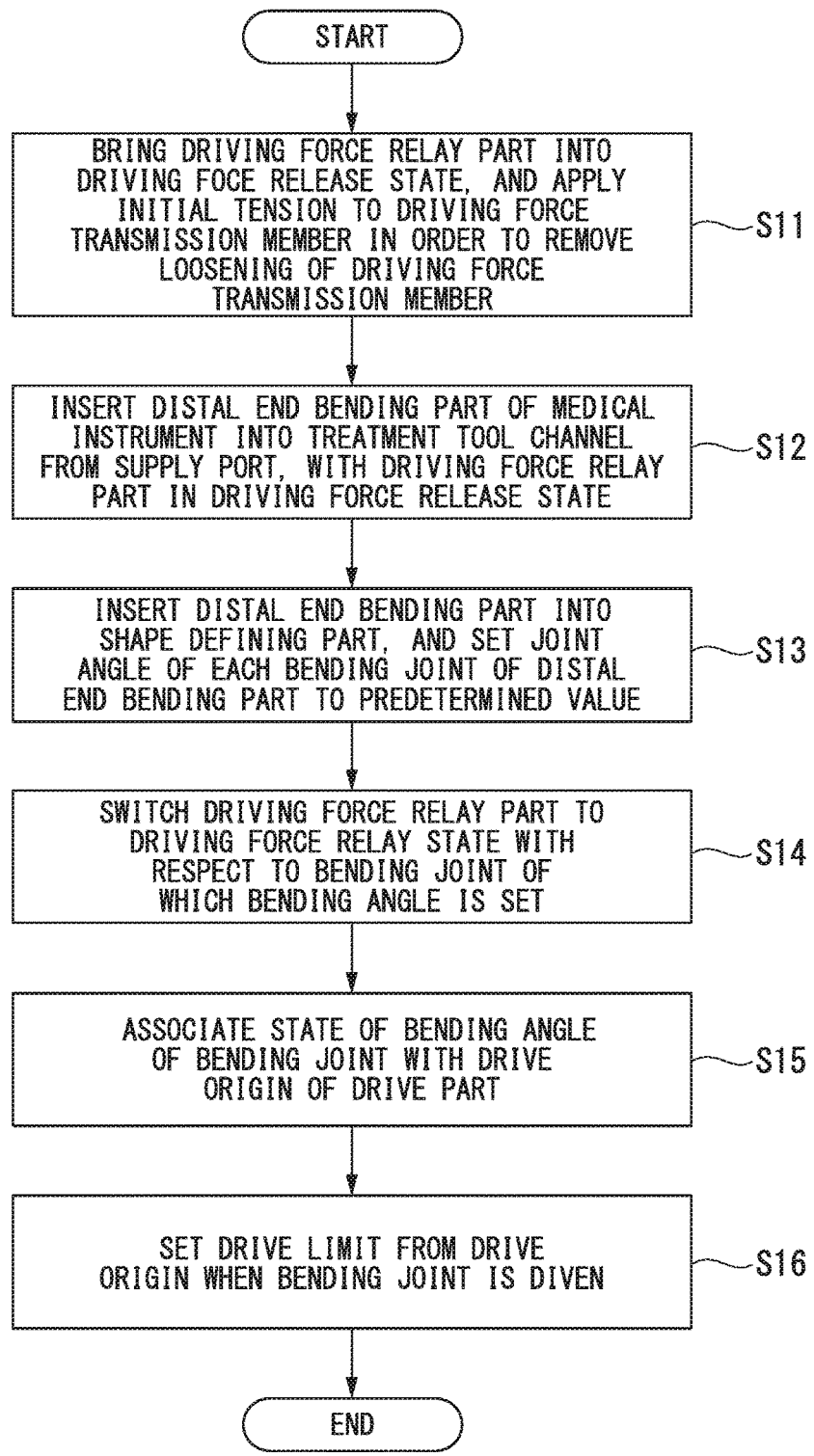

MANIPULATOR SYSTEM INITIALIZATION METHOD

CROSS REFERENCE TO RELATED APPLICATIONS

This application is a continuation application based on a PCT International Application No. PCT/JP2015/054763, filed on Feb. 20, 2015, whose priority is claimed on Japanese Patent Application No. 2014-032247, filed Feb. 21, 2014. Both of the contents of the PCT International Application and the Japanese Application are incorporated herein by reference.

BACKGROUND OF THE INVENTION

Field of the Invention

The present invention relates to a manipulator system initialization method.

Description of Related Art

In the related art, from the viewpoint of reducing stress of a patient, a treatment tool is inserted into a channel of an endoscope, the treatment tool is protruded from a distal end opening of the channel, and various kinds of treatment are performed under endoscope observation.

For example, Japanese Unexamined Patent Application, First Publication No. 2009-101077 describes, as such a manipulator system, a medical device consisting of an endoscope in which a bending part at a distal end is operable, and a treatment tool inserted through a treatment tool channel of the endoscope.

In this device, a treatment tool bending part that is operable from the outside is provided at the distal end of the treatment tool so that the treatment tool protruded from the endoscope can be actively bent. For this reason, when the operation of a treatment tool bending part is applied in addition to the operation of the bending part of the endoscope, the degree of freedom of the bending operation of the distal end of the treatment tool increases. Accordingly, the operating ability of a surgeon can be improved.

SUMMARY OF THE INVENTION

According to a first aspect of the invention, a manipulator system initialization method is provided for a manipulator system which includes: a medical instrument having a plurality of shaft-shaped parts coupled together by a bending joint, a driving force transmission part that transmits a driving force to the bending joint, a drive part that supplies the driving force to the driving force transmission part, and a driving force relay part capable of being switched between a driving force relay state where the driving force is relayed and a driving force release state where the driving force is cut off and the movement of the bending joint becomes free. The manipulator system initialization method includes a joint angle setting step of bringing the driving force relay part into the driving force release state, inserting the bending joint and a pair of the shaft-shaped parts coupled by the bending joint into a shape defining member having a shape defining part that brings the joint angle of the bending joint to a predetermined value, and setting the joint angle of the bending joint to the predetermined value; a drive part coupling step of switching the driving force relay part to the driving force relay state, with respect to the bending joint of which the joint angle is set; and an origin setting step of associating the state of the joint angle of the bending joint with the drive origin of the drive part after the drive part coupling step is performed.

According to a second manipulator system initialization method of the invention based on the above first aspect, a drive limit setting step of setting a drive limit from the drive origin when the bending joint is driven may be performed on the drive part after the origin setting step is executed.

According to a third manipulator system initialization method based on the above second aspect, in the drive limit setting step, the drive limit may be set by setting an allowable limit of a driving command value in a driving control unit that sends the driving command value from the drive origin to the drive part.

According to a fourth manipulator system initialization method based on any one aspect of the above first to third aspects, the drive part may include a position sensor for performing origin searching, and a drive part origin searching step of performing searching for the drive part origin, on the basis of a detection output of the position sensor until the driving force relay part is switched to the driving force relay state, may be executed in the origin setting step.

According to a fifth manipulator system initialization method based on any one aspect of the above first to fourth aspects, the driving force relay part may detachably couple the drive part to the driving force transmission part, may be brought into the driving force relay state at the time of coupling, and may be brought into the driving force release state at the time of decoupling.

According to a sixth manipulator system initialization method based on any one aspect of the above first to fourth aspects, the driving force relay part may be switched between the driving force relay state and the driving force release state according to the contact and separation of a clutch by coupling the drive part to the driving force transmission part via the clutch.

According to a seventh manipulator system initialization method based on any one aspect of the above first to sixth aspects, the driving force transmission part may include a linear driving force transmission member, and an initial tension applying step of applying an initial tension to the driving force transmission member in order to remove loosening of the driving force transmission member may be executed before the origin setting step is executed.

According to an eighth manipulator system initialization method based on any one aspect of the above first to seventh aspects, an insertion state determining step of detecting an insertion state where the bending joint and the shaft-shaped parts are inserted into the shape defining part, thereby determining whether or not setting of the joint angle with the shape defining part has succeeded, may be executed between the joint angle setting step and the drive part coupling step or in the middle of the joint angle setting step, and the joint angle setting step may be repeated, in a case where it is not determined that setting of the joint angle has succeeded.

According to a ninth manipulator system initialization method based on any one aspect of the above first to eighth aspects, a plurality of the bending joints may be provided, a plurality of the drive parts may be provided, and all of the plurality of bending joints and the plurality of drive parts may be initialized by repeating executing at least the joint angle setting step, the drive part coupling step, and the origin setting step on a bending joint capable of being inserted into the shape defining part among the plurality of bending joints while changing the bending joint to be inserted into the shape defining part.

BRIEF DESCRIPTION OF THE DRAWINGS

FIG. 5 is a flowchart illustrating the flow of the manipulator system initialization method of the first embodiment of the invention.

FIG. 6A is a schematic operation explanatory view of the manipulator system initialization method of the first embodiment of the invention.

FIG. 14 is a flowchart illustrating the flow of the manipulator system initialization method of the second embodiment of the invention.

DETAILED DESCRIPTION OF THE INVENTION

Hereinafter, embodiments of the invention will be described with reference to the accompanying drawings. In all the drawings, even in the case of different embodiments, the same reference signs will be given to the same or equivalent members, and common description will be omitted.

(First Embodiment)

A manipulator system used for a manipulator system initialization method of a first embodiment of the invention will be described.

Figure 1:
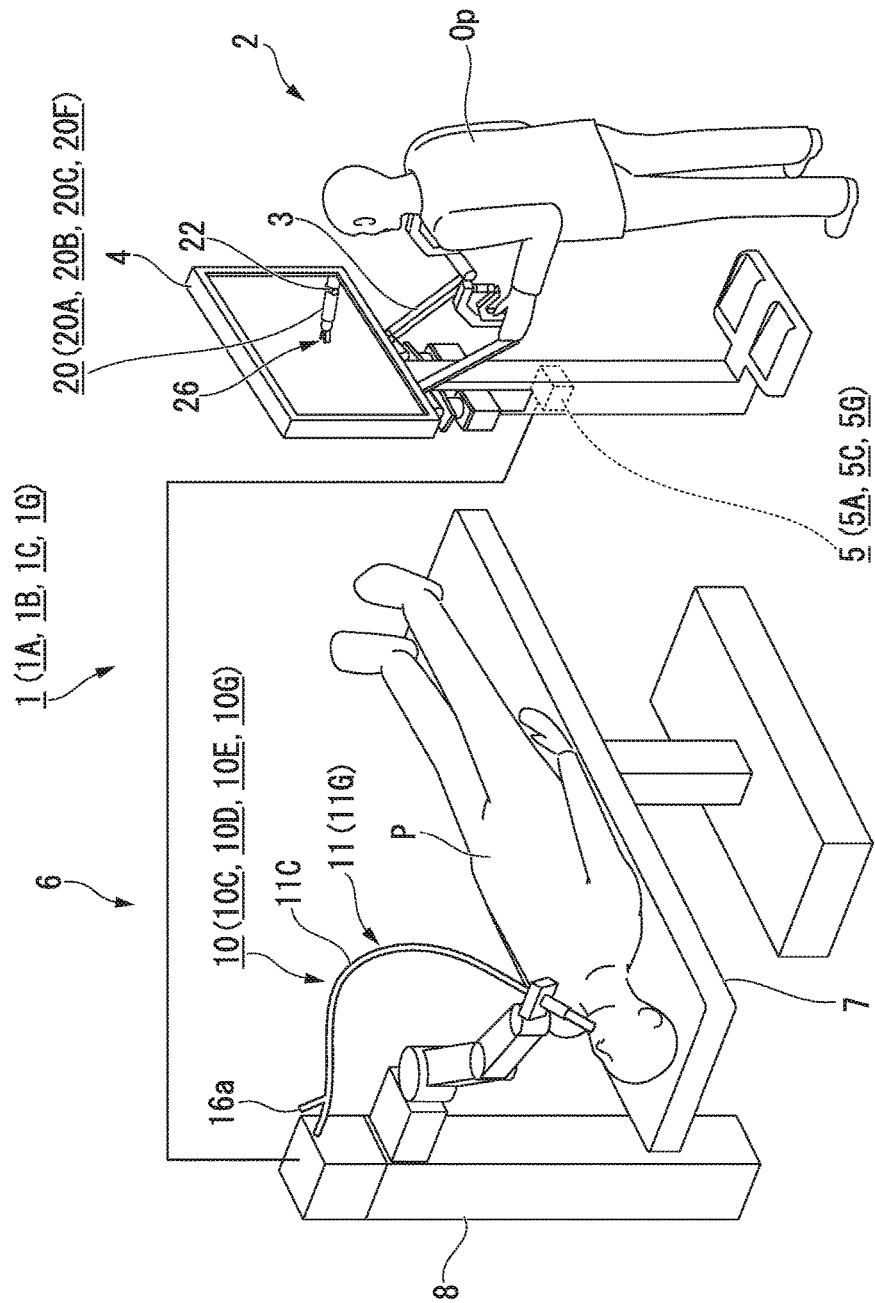
FIG. 1 is a schematic perspective view illustrating the overall configuration of a manipulator system used for a manipulator system initialization method of a first embodiment of the invention.
Figure 2:
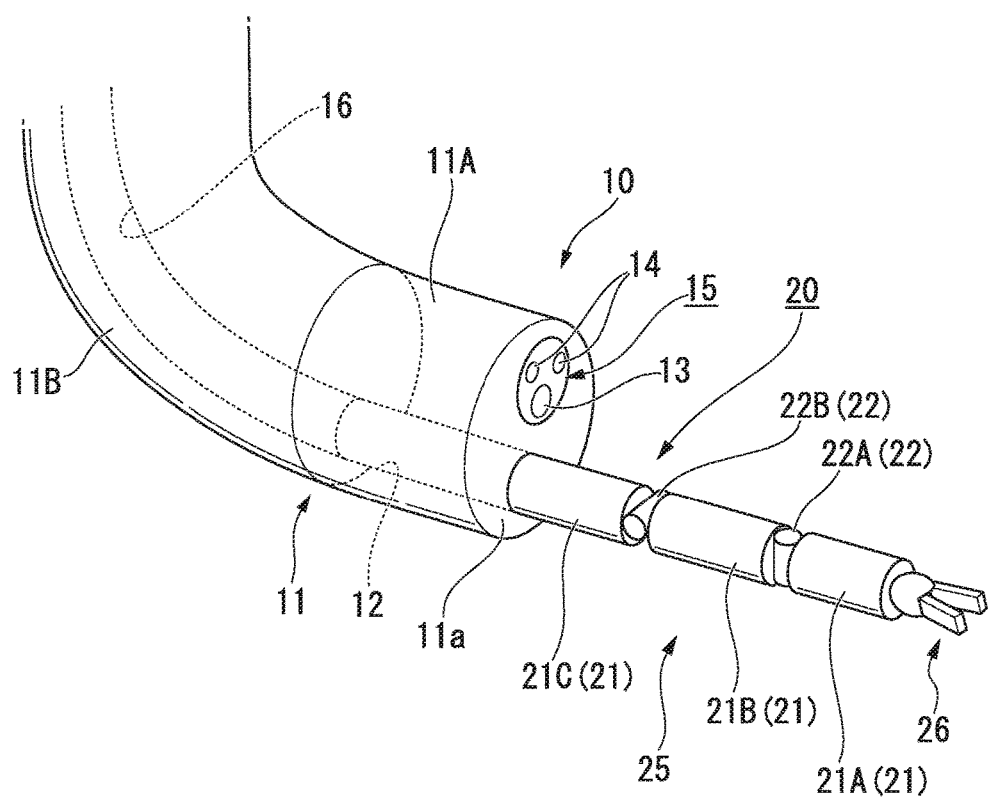
FIG. 2 is a schematic perspective view illustrating the external appearance of a shape defining member and a medical instrument used for the manipulator system initialization method of the first embodiment of the invention.
Figure 3A:
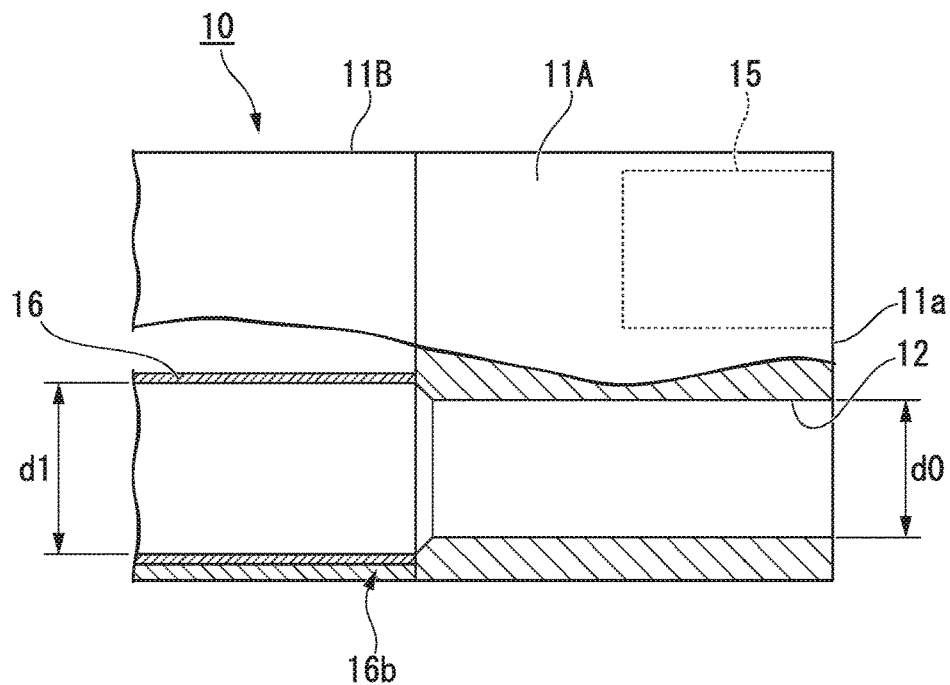
FIG. 3A is a partial sectional view of the shape defining member used for the manipulator system initialization method of the first embodiment of the invention.
Figure 3B:
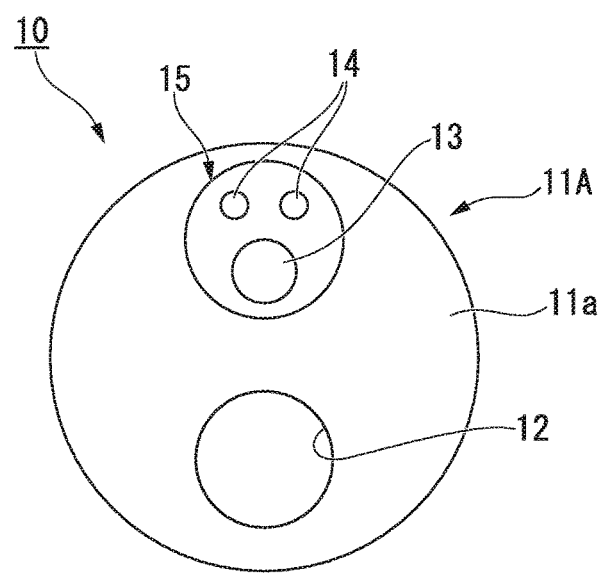
FIG. 3B is a right side view of FIG. 3A.
Figure 4:
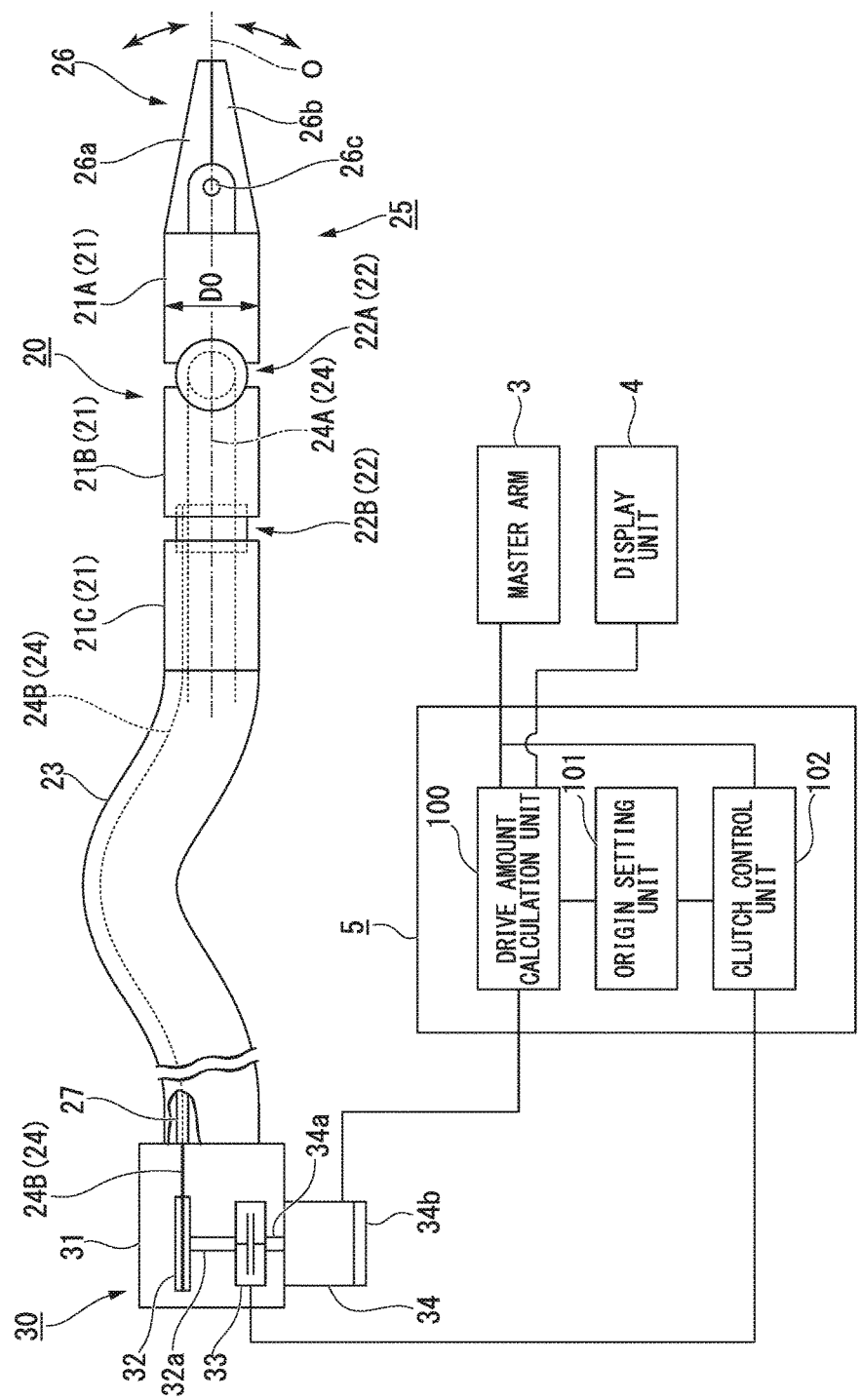
FIG. 4 is a schematic system configuration view of the medical instrument used for the manipulator system initialization method of the first embodiment of the invention.

FIG. 1 is a schematic perspective view illustrating the overall configuration of the manipulator system used for the manipulator system initialization method of the first embodiment of the invention. FIG. 2 is a schematic perspective view illustrating the external appearance of a shape defining member and a medical instrument used for the manipulator system initialization method of the first embodiment of the invention. FIG. 3A is a partial sectional view of the shape defining member used for the manipulator system initialization method of the first embodiment of the invention. FIG. 3B is a right side view in FIG. 3A. FIG. 4 is a schematic system configuration view of the medical instrument used for the manipulator system initialization method of the first embodiment of the invention.

In addition, since the respective drawings are schematic views, dimensions and shapes are exaggerated (the same applies to the following drawings).

As shown in FIG. 1, a manipulator system 1 of the present embodiment is a so-called master slave type system including a master manipulator 2 operated by an operator Op, and a slave manipulator 6 provided with an endoscope apparatus 10 for treatment.

The master manipulator 2 includes a master arm 3 with which the operator Op performs an operation input, a display unit 4 that displays an image captured using the endoscope apparatus 10 for treatment, and a control unit 5 that generates an operation command for operating the slave manipulator 6 on the basis of the operation of the master arm 3.

In the present embodiment, the master arm 3 is an operating part for operating respective parts of the slave manipulator 6 including a medical instrument 20 (manipulator) (to be described below) that is inserted into the endoscope apparatus 10 for treatment. Additionally, although not illustrated in detail, the master manipulator 2 has a pair of the master arms 3 corresponding to the right hand and left hand of the operator Op.

The master arm 3 has a joint structure in order to operate a manipulator having a bending joint with at least one degree of freedom like a bending part 11B of the endoscope apparatus 10 for treatment (to be described below) or joint parts 22 (bending joints) of the medical instrument 20.

Additionally, an end part of the master arm 3 located on the operator Op side is provided with a grasp operating part (not illustrated) for operating a grasping part 26 (to be described below) of the medical instrument 20.

The display unit 4 is a device on which an image of a treatment target part captured by an observation unit 15 (to be described below) attached to the endoscope apparatus 10 for treatment, an operation screen required for operation, the information from the control unit 5, and the like are displayed. The medical instrument 20 together with the treatment target part is also displayed on the display unit 4.

The slave manipulator 6 has the placement table 7 on which a patient P is placed, and a multi joint robot 8 arranged in the vicinity of the placement table 7.

The endoscope apparatus 10 for treatment is held by the multi joint robot 8. The medical instrument 20 that constitutes a portion of the slave manipulator 6 is allowed to be inserted through the endoscope apparatus 10 for treatment.

The multi joint robot 8, the endoscope apparatus 10 for treatment, and the medical instrument 20 operate according to an operation command issued from the master manipulator 2.

However, in the manipulator system of the invention, the multi joint robot is not indispensable, and for example, a configuration in which an assistant (not illustrated) holds the endoscope apparatus 10 for treatment may be adopted.

As illustrated in FIG. 2, the endoscope apparatus 10 for treatment has an overtube 11 that is an elongated member for being inserted into the body of the patient P. The overtube 11 includes a tubular insertion part 11C (refer to FIG. 1) having flexibility, the well-known bending part 11B equipped with, for example, a joint ring, a bending piece, and the like, and a distal end part 11A (shape defining member) formed of columnar hard resin, in this order toward a distal end from a proximal end.

The bending part 11B can change the orientation of the distal end part 11A by being bent by an operation input to the master arm 3. As a mechanism for bending the bending part 11B, for example, a well-known configuration in which driving wires inserted through inner peripheral surfaces of joint rings or bending pieces and fixed to the distal end part 11A can be inserted through the insertion part 11C and pulled with drive motors or the like on the proximal end side can be adopted.

A treatment tool channel 16 that is a path for supplying a treatment tool, such as the medical instrument 20, is provided inside the insertion part 11C and the bending part 11B.

A base end part (proximal end side) of the treatment tool channel 16, as illustrated in FIG. 1, is connected to a supply port 16a that opens to the side of the insertion part 11C.

A distal end part 16b of the treatment tool channel 16, as illustrated in FIG. 3A, passes through the distal end part 11A in an axial direction, and is connected to a base end side of a shape defining part 12 opening to a distal end surface 11a of the distal end part 11A.

The treatment tool channel 16 is formed of a flexible tubular member having an internal diameter d1.

In the present embodiment, the shape defining part 12 consists of a cylinder hole with a slightly smaller internal diameter d0 than the internal diameter d1 of the treatment tool channel 16. A method of setting the internal diameter d0 is described below.

As illustrated in FIGS. 2 and 3B, the observation unit 15 is a device for observing a treatment target part, and includes a well-known imaging mechanism 13 and a well-known illumination mechanism 14.

The imaging mechanism 13 and the illumination mechanism 14 are arranged inside the distal end part 11A, electrical wiring and optical fibers (not illustrated) are inserted through the inside of the bending part 11B and the inside of the insertion part 11C, and are coupled to an electric circuit and a light source in the control unit 5.

The imaging mechanism 13 and the illumination mechanism 14 have optical opening windows, in the distal end surface 11a of the distal end part 11A, and the outside light in front of the distal end part 11A can be received through the opening windows, or illumination light can be emitted forward therethrough.

In addition, although the observation unit 15 of the endoscope apparatus 10 for treatment is described in the present embodiment to be fixed to the distal end part of the overtube 11, the observation unit 15 may be movably provided.

For example, a channel for observation means is provided inside the overtube 11, and the observation unit is allowed to be moved forward and backward with respect to the overtube or to be bent by inserting an endoscope for observation having the observation unit at a distal end thereof through this channel for observation means.

The medical instrument 20 is an example of a manipulator that moves or drives an end effector at a distal end thereof by the bending joints, and is formed in the shape of an elongated shaft as a whole.

As illustrated in FIG. 4, the medical instrument 20 includes the joint parts 22 (bending joints) that are turned by the operation of the master arm 3, shaft-shaped parts 21 coupled to the joint parts 22, the grasping part 26 that grasps a treatment target or the like, a tubular part 23 having flexibility, and a drive unit 30 that supplies a driving force to the joint parts 22.

The grasping part 26 is an end effector of the medical instrument 20, and is attached to a distal end of the shaft-shaped part 21 located closest to the distal end side (distal end side).

The tubular part 23 is connected to the shaft-shaped part 21 closest to the base end side (proximal end side).

The joint parts 22 are bending joints, and the specific configuration thereof is not particularly limited if joints that transmit a driving force from a proximal end thereof using a driving force transmission member to perform bending are provided. The bending degree of freedom, the bending direction, the curvature, and the like in the joint parts 22 are not particularly limited.

In the following, joint parts having, sequentially from the proximal end side, a joint part 22B that is bent in a direction intersecting an extending direction of the medical instrument 20, and a joint part 22A that is bent in a direction orthogonal to the bending direction of the joint part 22B will be described as an example of the joint parts 22.

Both of the joint parts 22B and 22A have pulleys (not illustrated), and driving wires 24B and 24A are wound around the respective pulleys as driving force transmission members, and end parts thereof are fixed. In the following, the driving wires 24B and 24A are referred to as driving wires 24 in a case where the distinction therebetween is not particularly specified.

The shaft-shaped parts 21 have shaft-shaped parts 21B and 21C coupled by the joint part 22B, and a shaft-shaped part 21A coupled to the shaft-shaped part 21B by the joint part 22A.

For this reason, the shaft-shaped part 21C is a shaft-shaped part 21 located closest to the base end side in the medical instrument 20, and an end part thereof opposite to an end part to which the joint part 22B is connected is fixed to a distal end of the tubular part 23.

The shaft-shaped part 21A is a shaft-shaped part 21 located closest to the distal end side in the medical instrument 20, and the grasping part 26 is fixed to a distal end of the shaft-shaped part 21A that is an end part opposite to the joint part 22A.

The joint parts 22B and 22A are coupled to both end parts of the shaft-shaped part 21B.

In the following, a coupling body consisting of the shaft-shaped part 21C, the joint part 22B, the shaft-shaped part 21B, the joint part 22A, the shaft-shaped part 21A, and the grasping part 26 is referred to as a distal end bending part 25.

Each shaft-shaped part 21 has an external diameter D0 such that the shaft-shaped part is insertably fitted into an internal diameter d0 of the shape defining part 12 of the distal end part 11A.

Each joint part 22 is formed with a size such that the joint part does not protrude more than the outer shape of a coupled shaft-shaped part 21.

The internal diameter d0 of the shape defining part 12 is set so as to become a predetermined value where the joint angle of each joint part 22 falls within a range of constant variation, in consideration of the insertion length of the shaft-shaped parts 21, when the joint part 22 and a pair of the shaft-shaped parts 21 coupled by the joint part 22 are inserted into the shape defining part 12.

For example, in the present embodiment, the shape defining part 12 has a cylindrical shape. Therefore, if d0=D0 is established, each shaft-shaped part 21 is aligned coaxially with a straight axis O, and the joint angle of the joint part 22 becomes an angle that brings the angle formed between the shaft-shaped parts 21 adjacent to each other to 180°. In a case where the internal diameter d0 is greater than the external diameter D0, the joint angle becomes an angle within a certain range of about 180° according to a difference therebetween.

Since the magnitude of such a setting variation of the joint angle becomes a setting miscalculation of a drive origin, and becomes a movement position error of the grasping part 26, the internal diameter d0 is determined so as to become an allowable magnitude in terms of the operation of the medical instrument 20.

The grasping part 26 has a pair of grasping members 26a and 26b for holding the treatment tool, and a turning shaft 26c that turnably supports the grasping members 26a and 26b. By operating the grasp operating part (not illustrated) of the master arm 3, the grasping members 26a and 26b are turned around the turning shaft 26c, and is moved and operated for opening and closing like the arrow of FIG. 4.

Transmission means for transmitting the driving force of the grasping part 26 is not particularly limited, and for example, means for driving a link (not illustrated) coupled to the grasping members 26a and 26b with an operating wire is possible.

The grasping part 26, as illustrated in FIG. 4, has a size such that the grasping part does not protrude more than the outer shape of the coupled shaft-shaped part 21, in a case where the grasping part is closed without grasping an object to be grasped.

For this reason, the distal end bending part 25 is in a straightly extending state, becomes a shaft-shaped body in which the maximum external diameter is D0 in a state where the grasping part 26 is closed as described above, and has a shape such that the distal end bending part is insertable into the shape defining part 12 so as to be advanceable and retractable.

The tubular part 23 consists of, for example, a tubular member, such as a resin tube, and has insertion objects, such as the driving wires 24A and 24B for driving the joint parts 22A and 22B, respectively, inserted thereinto.

The driving wires 24A and 24B are inserted through the inside of sheaths 27 of which both end parts are fixed from a base end part of the tubular part 23 to the vicinity of a pulley at the distal end.

Each sheath 27 is formed of a densely wound coil or the like that has almost the same diameter as the internal diameter of each driving wire 24. Accordingly, even if the sheath receives an external force and is bent, the length thereof rarely varies. However, the internal diameter of the sheaths 27 is slightly greater than the external diameter of the driving wires 24 in order to smoothly pull the driving wires 24.

Although the illustration of insertion objects other than the driving wires 24A and 24B is omitted, the insertion objects may include examples, such as the operating wire for driving the grasping part 26, the electrical wiring connected to the observation unit 15, the optical fibers, and the like.

The drive unit 30 includes a driving mechanism part 31 (driving force transmission part) fixed to the base end part of the tubular part 23, and a drive motor 34 (drive part) that supplies a driving force.

The driving mechanism part 31 includes a drive pulley 32 that is rotated and supported by a rotating shaft 32a and has each driving wire 24 wound therearound, and a clutch 33 (driving force relay part) provided between an output shaft 34a of the drive motor 34 and the rotating shaft 32a in order to perform relay control of the driving force generated by the drive motor 34.

The type of drive motor 34 is not particularly limited if only the output shaft 34a can be rotated by an amount of rotation on the basis of a driving command value. For example, a servo motor, a stepping motor, a DC motor, and the like can be adopted.

In the present embodiment, the drive motor 34 has an encoder 34b that detects the rotational amount of the output shaft 34a, and is communicably connected to the control unit 5 that controls the driving of the drive motor 34 on the basis of the operation of the master arm 3.

The clutch 33 is a driving force relay part that is switched between a driving force relay state where a driving force is relayed when the rotating shaft 32a is coupled to the output shaft 34a of the drive motor 34 and is rotated by the same rotational amount as that of the output shaft 34a, and a driving force release state where a driving force is cut when the rotating shaft 32a is cut off from the output shaft 34a.

The type of clutch 33 may be a mechanical clutch mechanism, or may be an electrical clutch mechanism, such as an electromagnetic clutch.

As the switching operation (hereinafter, simply referred to as switching operation in a case where there is no concern of misunderstanding) between the driving force relay state and the driving force release state by the clutch 33, for example, switching using a manual switch provided in the driving mechanism part 31 or the like is possible. In the present embodiment, the clutch 33 is communicably connected to the control unit 5, and a switching operation is performed on the basis of a control signal sent from the control unit 5 on the basis of the operation of the master arm 3.

The driving mechanism part 31 and the drive motor 34 are provided to correspond to each joint part 22 of the distal end bending part 25, although only portions thereof are illustrated in FIG. 4.

For this reason, a switching operation is independently possible for each joint part 22, and in a case where switching to the driving force relay state is performed, the respective amounts of driving can be independently changed.

In the drive unit 30 of the present embodiment, each driving wire 24, the drive pulley 32, and the rotating shaft 32a constitute the driving force transmission part that transmits a driving force to each bending joint.

Next, with respect to the functional configuration of the control unit 5, the functional configuration of portions (driving control unit) that controls the driving of each joint part 22 will mainly be described.

The control unit 5 includes a drive amount calculation unit 100, an origin setting unit 101, and a clutch control unit 102, as a driving control unit.

The drive amount calculation unit 100 analyzes the movement of the joint part of the master arm 3 sent from the master arm 3 to calculate the rotational angle of each joint part 22 for performing the same operation, and sends a corresponding driving command value to each drive motor 34 that drives each joint part 22.

The origin setting unit 101 sets the origin of the driving command value, which is sent to the drive motor 34 by the drive amount calculation unit 100, to the drive amount calculation unit 100.

In the present embodiment, the timing of such origin setting by the origin setting unit 101 is necessarily performed at a timing at which the clutch 33 is switched from the driving force release state to the driving force relay state by the clutch control unit 102.

For this reason, the origin setting unit 101 is communicably connected to the drive amount calculation unit 100 and the clutch control unit 102.

In the present embodiment, if the origin setting unit 101 sets the origin, a drive limit to each joint part 22 is set.

This drive limit is determined in advance with respect to each joint part 22, and the origin setting unit 101 soft-sets each drive limit in the drive amount calculation unit 100 communicably connected thereto.

The drive amount calculation unit 100 performs the operation of determining whether or not the driving command value exceeds the drive limit before the driving command value is sent to the drive motor 34.

In a case where the driving command signal is determined to exceed the drive limit, the drive amount calculation unit 100 stops the driving of the drive motor 34, and displays information, capable of knowing that the driving command value exceeds the drive limit, on the display unit 4.

The clutch control unit 102 is provided to operate the switching operation of the clutch 33 by remote control on the basis of the operation of the master arm 3, and is communicably connected to the clutch 33 and the origin setting unit 101.

The clutch control unit 102 notifies the origin setting unit 101 of the operation of the clutch 33 being performed when the clutch 33 is switched from the driving force release state to the driving force relay state.

The device configuration of such a control unit 5 consists of a computer consisting of a CPU, a memory, an input/output interface, an external storage, and the like, and thereby, a suitable control program that realizes the control functions as above is executed.

Next, the manipulator system initialization method of the present embodiment in the medical instrument 20 of such a manipulator system 1 will be described.

Figure 6B:
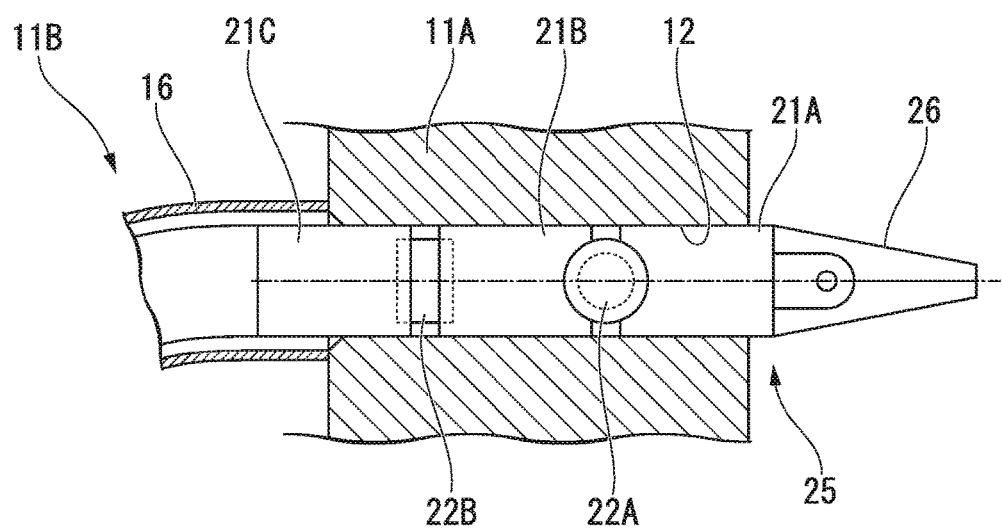
FIG. 6B is a schematic operation explanatory view of the manipulator system initialization method of the first embodiment of the invention.

FIG. 5 is a flowchart illustrating the flow of the manipulator system initialization method of the first embodiment of the invention. FIGS. 6A and 6B are schematic operation explanatory views of the manipulator system initialization method of the first embodiment of the invention.

In order to perform treatment using the medical instrument 20 of the manipulator system 1, first, it is necessary to insert the distal end part of the medical instrument 20 into the body of the patient P at a treatment target part, using the overtube 11, and to advance the distal end part to the vicinity of the treatment target part.

Additionally, in order to precisely operate the medical instrument 20 by the master arm 3, it is necessary to associate the joint angle of each joint part 22 with the drive origin of the drive motor 34 in a state where the joint angle reaches a constant value.

If the association of the drive origin is performed before being inserted into the overtube 11 or before the overtube 11 is inserted into the body even after insertion into the overtube 11, the bending operation of the distal end bending part 25 is also should be performed according to the bending of the overtube 11. Therefore, operating ability deteriorates, and substantial time is taken.

In the manipulator system initialization method of the present embodiment, an initialization operation including the association of the drive origin of the medical instrument 20 after the overtube 11 is inserted into the body of the patient P is performed.

Specifically, Steps S1 to S5 of FIG. 5 are executed according to the flow illustrated in FIG. 5.

First, Step S1 is performed. This step is a step of inserting the distal end bending part 25 of the medical instrument 20 into the treatment tool channel 16 from the supply port 16a, with the clutch 33 that is the driving force relay part being brought into the driving force release state.

The operator Op performs an operation input of bringing the clutch 33 into the driving force release state, using the master arm 3. Accordingly, the clutch control unit 102 of the control unit 5 sends a control signal to the clutch 33, and brings the clutch 33 into the driving force release state.

Accordingly, since each joint part 22 of the distal end bending part 25 is brought into a state where the joint part is easily bent if an external force is applied, and the tubular part 23 originally has flexibility, the medical instrument 20 becomes bendable. For this reason, even if the treatment tool channel 16 is bent when the overtube 11 is bent, the medical instrument 20 can be smoothly inserted into the treatment tool channel 16.

When the insertion of the medical instrument 20 proceeds, and as illustrated in FIG. 6A, the distal end bending part 25 reaches the distal end part 16b of the treatment tool channel 16, the insertion is stopped.

The above completes Step S1.

In this way, in the medical instrument 20 inserted in the treatment tool channel 16, the distal end bending part 25 and the tubular part 23 can be bent together with the treatment tool channel 16.

Therefore, Step S1 can be performed before the overtube 11 is inserted into the body of the patient P, or can also be performed even after the overtube 11 is inserted into the body of the patient P.

In a case where the medical instrument 20 is used at the beginning of treatment, it is efficient if the distal end bending part 25 is inserted up to the distal end part 16b of the treatment tool channel 16 before the overtube 11 into the body of the patient P.

In a case where treatment is performed using the medical instrument 20 after other treatment is performed, it is efficient to insert the medical instrument 20 into the treatment tool channel 16 in a state where the overtube 11 is left inside the body of the patient P after other treatment tools are extracted.

Next, Step S2 is performed. This step is a step of inserting the distal end bending part 25 into the shape defining part 12 and setting the joint angle of each joint part 22, which is a bending joint of the distal end bending part 25, to a predetermined value.

If the medical instrument 20 is further inserted from the state illustrated in FIG. 6A to the distal end side, the distal end bending part 25 is inserted into the shape defining part 12, with the grasping part 26 as a head.

The internal diameter d0 of the shape defining part 12 is slightly greater than the external diameter D0 of the distal end bending part 25. For this reason, for example, even if the shaft-shaped parts 21A and 21B coupled to the joint part 22A are being bent within the treatment tool channel 16, the shaft-shaped parts 21A and 21B are moved and are fitted along an inner peripheral surface of the shape defining part 12, and is aligned straight within a constant allowable range.

Accordingly, the joint angle of the joint part 22A is a predetermined angle that brings the angle between the shaft-shaped parts 21A and 21B to substantially 180° (including the case of 180°).

Similarly, if the joint part 22B, and the shaft-shaped part 21C and the shaft-shaped part 21B that are coupled to the joint part 22B are inserted into the shape defining part 12, the joint angle of the joint part 22B becomes the same predetermined angle as the joint part 22A.

In the present embodiment, as illustrated in FIG. 6B, if all the joint parts 22 of the distal end bending part 25 and at least some of the shaft-shaped parts 21 coupled thereto are inserted into the shape defining part 12, the operator Op stops the insertion of the medical instrument 20.

The above completes Step S2.

Since the treatment tool channel 16 is often bent in the state of insertion of the overtube 11 and the medical instrument 20, the path length of each driving wire 24 between the driving mechanism part 31 and each joint part 22 is different from, for example, a path length in a case where the medical instrument 20 is brought into the straight state, depending on a bent state. For this reason, the rotational position of the drive pulley 32 varies according to a difference between the path lengths of mutually facing wire portions of the driving wires 24 stretched between the pulleys of the joint parts 22.

However, in this step, since the clutch 33 is in the driving force release state, the drive pulley 32 can be freely rotated.

The above Step S2 constitutes a joint angle setting step of bringing the driving force relay part into the driving force release state, inserting a bending joint and a pair of shaft-shaped parts coupled together by the bending joint into the shape defining member, and setting the joint angle of the bending joint to a predetermined value.

Next, Step S3 is performed. This step is a step of switching the clutch 33 to the driving force relay state, with respect to the joint part 22 of which the joint angle is set.

The operator Op performs an operation input of bringing the clutch 33 into the driving force relay state, using the master arm 3. Accordingly, the clutch control unit 102 of the control unit 5 sends a control signal to the clutch 33, and brings the clutch 33 into the driving force relay state.

When the clutch 33 is switched to the driving force relay state, the clutch control unit 102 notifies the origin setting unit 101 of the clutch 33 being switched to the driving force relay state.

Accordingly, the output shaft 34a of the drive motor 34 and the rotating shaft 32a are brought into a coupled state, and the rotational position of the drive pulley 32 connected to the rotating shaft 32a interlocks with the rotation of the drive motor 34.

For this reason, unless the drive motor 34 is driven, the joint angle of each joint part 22 in the distal end bending part 25 is maintained at the joint angle when being switched to the driving force relay state. For example, if the medical instrument 20 is further moved to the distal end side, the distal end bending part 25 maintains the straight state, and protrudes to the front of the distal end part 11A.

The above completes Step S3.

The above Step S3 constitutes a drive part coupling step of switching the driving force relay part to the driving force relay state, with respect to the bending joint of which the joint angle is set.

Next, Step S4 is performed. This step is a step of associating the state of the joint angle of each joint part 22 with the drive origin of each drive motor 34.

The origin setting unit 101 notified of the clutch 33 being switched to the driving force relay state sends a control signal that sets the origin of a driving command value, which is sent to each drive motor 34 by the drive amount calculation unit 100 sends, to the rotational position of the current drive motor 34. Accordingly, the drive amount calculation unit 100 calculates the amount of driving by recognizing the rotational position of each current drive motor 34 as a drive origin.

The above completes Step S4.

The above Step S4 constitutes an origin setting of associating the state of the joint angle of the bending joint with the drive origin of the drive part after the drive part coupling step is performed.

Next, Step S5 is performed. This step is a step of setting the drive limit from the drive origin when each joint part 22 is driven.

If the origin of the driving command value is set in the above Step S4, the origin setting unit 101 sends a driving command value corresponding to the drive limit, which is determined in advance with respect to each joint part 22, to the drive amount calculation unit 100, and stores the driving command value in the drive amount calculation unit 100.

For example, even in a case where the movable range of the joint part 22 is ±X0 from the origin at the driving command value, an operationally required driving range of the medical instrument 20 is only ±X (where, X<X0) in many cases. If the joint part is allowed to move beyond this movable range, the joint part may interfere with other treatment tools or instruments in the body of the patient P in a case where an operation is excessively and erroneously performed. Moreover, the load applied to each driving wire 24 may become excessive, and the driving wire and the manipulator may be damaged.

For this reason, in the present embodiment, for example, the above driving command value X is stored as the drive limit in the drive amount calculation unit 100.

The above completes Step S5, and the manipulator system initialization method of the present embodiment with respect to the medical instrument 20 is completed.

The above Step S5 constitutes a drive limit setting step of setting the drive limit from the drive origin when the bending joint is driven, with respect to the drive part, and is a drive limit setting step using soft setting of setting the drive limit by setting the allowable limit of the driving command value, particularly in the driving control unit that sends the driving command value from the drive origin to the drive part.

If the initialization is completed in this way, it is possible to start suitable treatment.

For example, the operator Op causes the distal end bending part 25 of the medical instrument 20 to protrude from the overtube 11 while checking an image of a surgical field acquired by the observation unit 15, with the display unit 4.

In this case, when the tubular part 23 moves inside the treatment tool channel 16, the curved shape of the driving wire 24 changes slightly. However, since the entire length of the distal end bending part 25 is sufficiently short compared to the entire length of the tubular part 23, the path length of the driving wire 24 hardly varies in the change of the curved shape caused by the movement required to cause the distal end bending part 25 to protrude. Therefore, the distal end bending part 25 protrudes in a state where the joint angle of each joint part 22 is kept constant, and maintains a straightly extending state in the present embodiment.

The operator Op performs a predetermined operation input for operating the master arm 3 to bend the distal end bending part 25 of the medical instrument 20 or grasping the treatment part or the like with the grasping part 26, according to the necessary of a treatment operation, while viewing the image of the surgical field by the display unit 4.

For example, if the operation input of bending the distal end bending part 25 is performed, the drive amount calculation unit 100 of the control unit 5 analyzes the operation input of the master arm 3 to obtain the joint angle of each joint part 22 and realizes a bent state that is input for operation, and calculates a driving command value with respect to each drive motor 34 that transmits a driving force to each joint part 22, according to each joint angle.

The drive amount calculation unit 100 determines whether or not each driving command value exceeds the drive limit, and sends each driving command value to each drive motor 34 in a case where all driving command values are within a range of the drive limit.

In a case where a driving command value exceeding the drive limit is present, the drive amount calculation unit 100 stops the sending of each driving command value, and causes the display unit 4 to display a message of warning that the driving command value exceeds the drive limit on the display unit 4. The operator Op views the message of the display unit 4, and changes the operation input of the master arm 3.

In addition, displaying the warring message on the display unit 4 is an example. As warning means, means other than the display of a message can also be adopted. For example, an alarm sound may be generated to issue a warning, and the generation of alarm sound and the display to the display unit 4 may be used together.

When the driving command value is sent to each drive motor 34, each drive motor 34 rotates and the drive pulley 32 rotates. Accordingly, the driving wire 24 wound around the drive pulley 32 is pulled in an appropriate direction, and rotates the pulley of the joint part 22 that transmits a driving force.

In this way, the joint part 22 is driven, and the distal end bending part 25 is bent on the basis of the operation of the master arm 3.

After the treatment operation is completed, the operator Op performs, for example, the operation of returning each joint part 22 of the distal end bending part 25 to the origin from the master arm 3. Accordingly, since the distal end bending part 25 is aligned in a straight state, the distal end bending part 25 can be pulled back to the base end side, and can be housed inside the shape defining part 12.

Additionally, such origin return may not be performed, and the operation of pulling back the distal end bending part 25 after being switched to the driving force release state may simply be performed. In this case, since the rotation of each joint part 22 becomes free, the distal end bending part 25 is passively housed inside the shape defining part 12.

In a case where the medical instrument 20 is extracted independently or together with the overtube 11 from the body of the patient P, the operation of the medical instrument after the clutch 33 is switched to the driving force release state is performed.

According to the manipulator system initialization method of the present embodiment, the initialization operation is performed by inserting the distal end bending part 25 in the driving force release state into the shape defining part 12 of the distal end part 11A that is the shape defining member provided at the distal end part of the overtube 11.

For this reason, even if the treatment tool channel 16 is bent, the medical instrument 20 can be smoothly inserted.

Additionally, in this method, the distal end bending part 25 is inserted into the shape defining part 12 after the sheath 27 and the driving wire 24 of the medical instrument 20 are bent in imitation of the bent state of the treatment tool channel 16, the shape of the distal end bending part 25 is defined, and the drive origin is set in this state.

For this reason, as long as the bent state of the treatment tool channel 16 is maintained, an orientation defined by the shape defining part 12 can be precisely reproduced as the orientation of the distal end bending part 25 in the origin regardless of the bent state.

For this reason, the precise bending operation of the distal end bending part 25 can be performed.

Additionally, in the present embodiment, the drive limit is set, and thus the distal end bending part 25 is not excessively bent. Therefore, an excessive load can be prevented from being applied to the medical instrument 20 or a medical treatment target.

(First Modification Example)

Next, a manipulator system initialization method of a modification example (first modification example) of the above first embodiment will be described.

Figure 7:
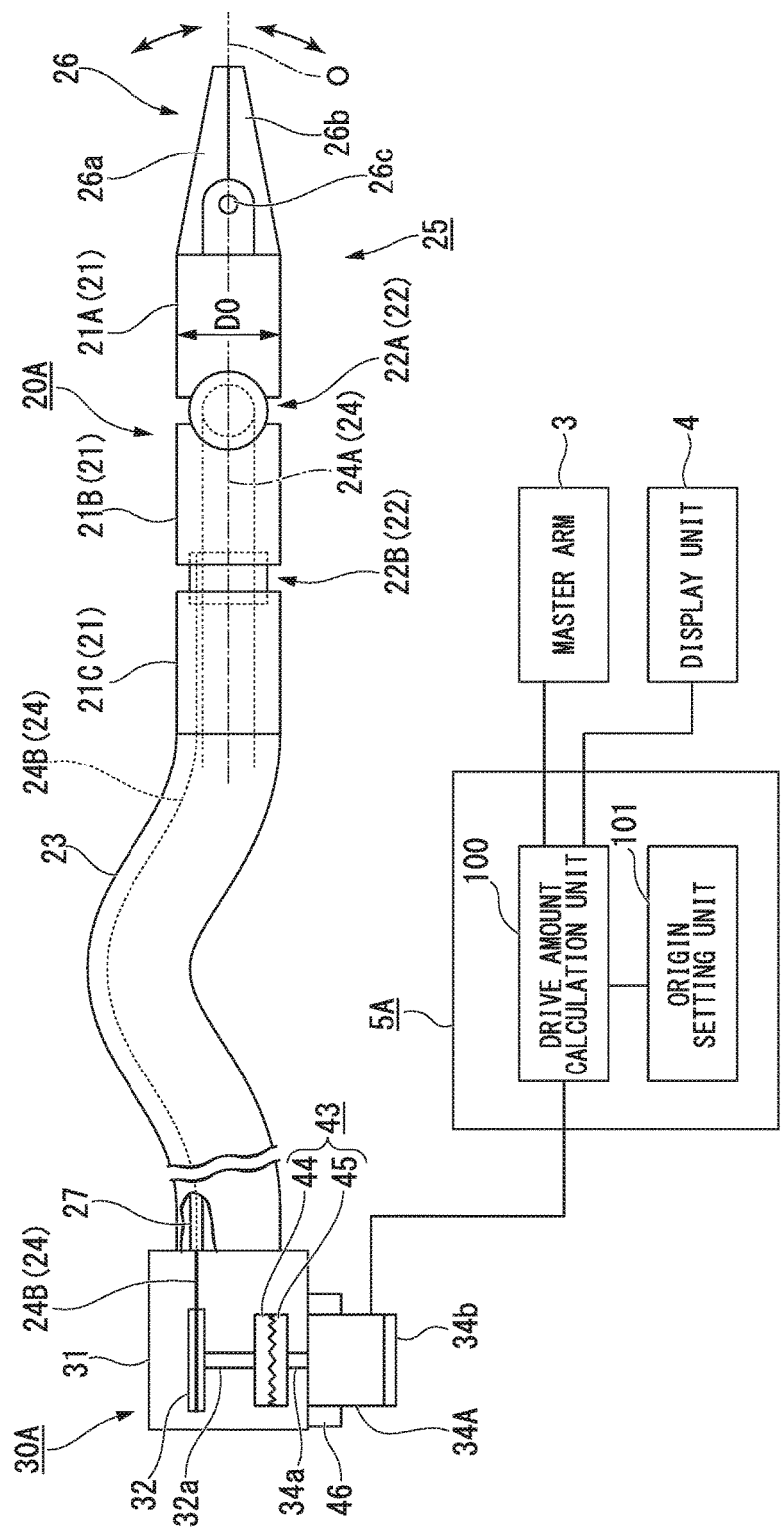
FIG. 7 is a schematic system configuration view of a medical instrument used for a manipulator system initialization method of a modification example (first modification example) of the first embodiment of the invention.
Figure 8A:
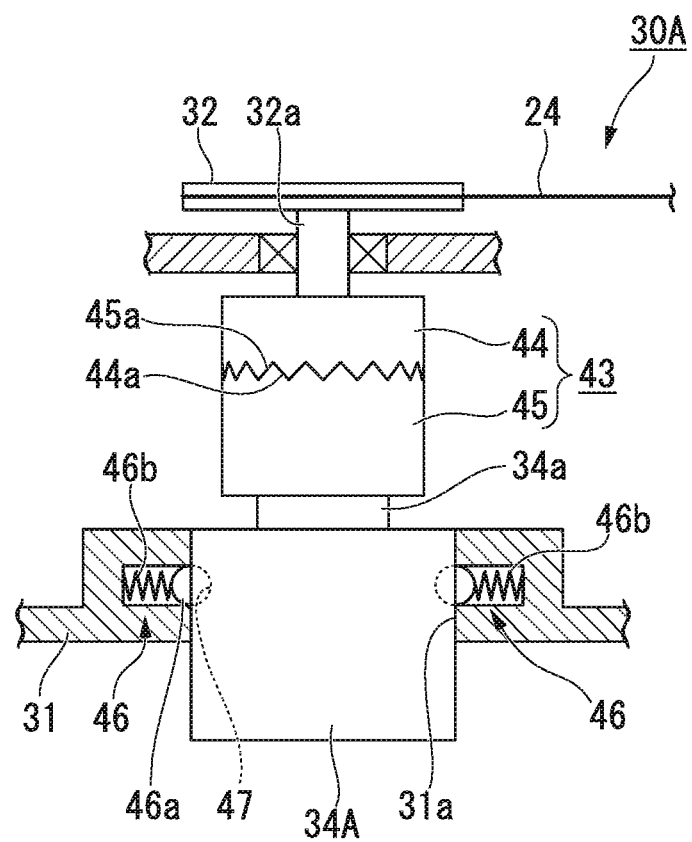
FIG. 8A is a schematic sectional view illustrating the configuration of a drive unit of the medical instrument used for the initialization method of the manipulator system initialization method of the modification example (first modification example) of the first embodiment of the invention.
Figure 8B:
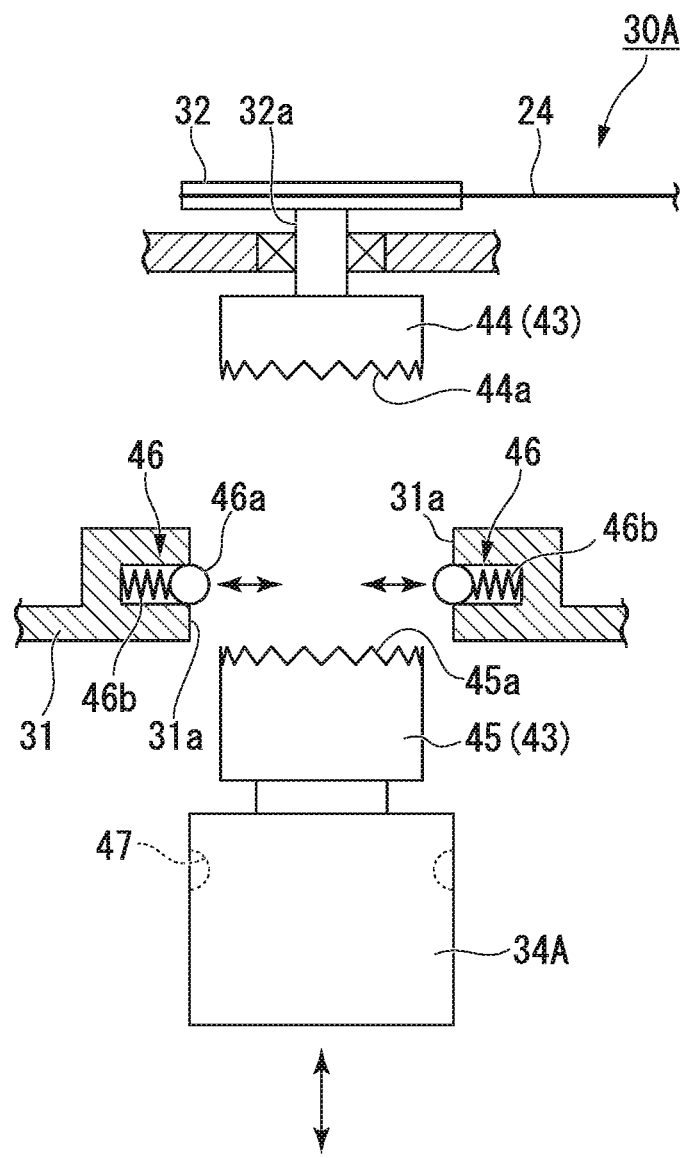
FIG. 8B is a schematic sectional view illustrating the configuration of the drive unit of the medical instrument used for the initialization method of the manipulator system initialization method of the modification example (first modification example) of the first embodiment of the invention.

FIG. 7 is a schematic system configuration view of a medical instrument used for the manipulator system initialization method of the modification example (first modification example) of the first embodiment of the invention. FIGS. 8A and 8B are schematic sectional views illustrating the configuration of a drive unit of the medical instrument used for the initialization method of the manipulator system initialization method of the modification example (first modification example) of the first embodiment of the invention.

As illustrated in FIG. 1, a manipulator system 1A used for the manipulator system initialization method of the present modification example includes a medical instrument 20A (manipulator) and a control unit 5A (driving control unit), instead of the medical instrument 20 and the control unit 5 of the manipulator system 1 in the above first embodiment.

Hereinafter, differences from the above first embodiment will mainly be described.

As illustrated in FIG. 7, the medical instrument 20A includes a drive unit 30A, instead of the drive unit 30 of the medical instrument 20 of the above first embodiment.

The drive unit 30A includes an attachment/detachment part 43 (driving force relay part) and a drive motor 34A (drive part), instead of the clutch 33 and the drive motor 34 of the drive unit 30, and is obtained by adding a fixing part 46 to a housing of the driving mechanism part 31.

The attachment/detachment part 43, as illustrated in FIGS. 8A and 8B, includes a fixed-side receiving member 44 fixed to the rotating shaft 32*a*, and a mounting member 45 fixed to the output shaft 34*a*.

The fixed-side receiving member 44 and the mounting member 45 are substantially disk-shaped members, and includes concavo-convex coupling surfaces 44*a* and 45*a* consisting of a concavo-convex shape, which are fitted to each other without sliding at least in a circumferential direction, on mutually facing surfaces thereof.

As the shape of the concavo-convex coupling surface 44*a* (45*a*), for example, a shape in which a plurality of protrusions having a chevron-shaped cross-section radially extend with respect to the center of the fixed-side receiving member 44 (mounting member 45) and are arranged adjacent to each other in the circumferential direction can be adopted.

The drive motor 34A is different from the drive motor 34 in that the mounting member 45 is fixed to a distal end of the output shaft 34*a* and in that a side surface of the drive motor is provided with a fitting concave part 47 for allowing a fitting projection 46*a* advanced and retracted from the fixing part 46 (to be described below) to be fitted thereinto.

The fixing part 46 is a device part in which the drive motor 34A is detachably fixed to the housing of the driving mechanism part 31. FIG. 8A illustrates a state where the drive motor 34A is mounted on the fixing part 46, and FIG. 8A illustrates a state where the drive motor 34A is detached from the fixing part 46.

The specific configuration of the fixing part 46 is not particularly limited if the fixing part 46 can fix the drive motor 34A in a positional relationship in which the concavo-convex coupling surface 45*a* of the mounting member 45 is fitted to the concavo-convex coupling surface 44*a* of the fixed-side receiving member 44 inside the driving mechanism part 31 when the drive motor 34A is mounted.

In the present modification example, as an example, a configuration includes a hole 31*a* provided in the housing of the driving mechanism part 31 and fitted to the side surface of the drive motor 34A, and a fitting projection 46*a* provided on an inner peripheral surface of the hole 31*a* so as to be advanceable and retractable.

As illustrated in FIG. 8A, the fitting projection 46*a* is provided in a shape such that the fitting projection 46*a* is fitted to the fitting concave part 47 of the drive motor 34A, and is biased toward the center of the hole 31*a* by a biasing member 46*b*.

Various spring members or elastic members can be used as the biasing member 46*b*.

In addition, it is not indispensable to individually detach and attach the drive motor 34A in this way. For example, in a case where a plurality of the drive motors 34A are provided, a configuration in which a holding member that integrally holds the plurality of drive motors 34A is provided, and the holding member is attachable to and detachable from a suitable fixing part provided in the driving mechanism part 31 is also possible. In this case, the plurality of drive motors 34A are simultaneously detached and attached.

The control unit 5A is different from the drive unit 30A in which the clutch control unit 102 of the control unit 5 of the above first embodiment is eliminated so as to correspond to not having the clutch 33.

By virtue of such a configuration, the drive motor 34A is detachably fixed to the hole 31*a* of the driving mechanism part 31 via the fixing part 46.

As illustrated in FIG. 8A, the position of the drive motor 34A is fixed in the axial direction and the circumferential direction by the fitting projection 46*a* of the fixing part 46 being fitted to the fitting concave part 47 of the drive motor 34A in a state where the drive motor 34A is mounted.

In such a mounting state, the fixed-side receiving member 44 and the mounting member 45 of the attachment/detachment part 43 are fitted to each other in the axial direction and the circumferential direction in the concavo-convex coupling surfaces 44*a* and 45*a*.

For this reason, if the drive motor 34A is driven, the rotation of the output shaft 34*a* is transmitted to the rotating shaft 32*a* via the attachment/detachment part 43. Therefore, the attachment/detachment part 43 is brought into the driving force relay state.

As illustrated in FIG. 8B, if the drive motor 34 is pulled to the outside of the driving mechanism part 31 in the axial direction, the fitting projection 46*a* is pushed out radially outward from the fitting concave part 47 and the drive motor 34A is extracted, so that the drive motor 34A can be detached from the fixing part 46.

In such a detachment state, the attachment/detachment part 43 are separated into the fixed-side receiving member 44 and the mounting member 45, and the mounting member 45 is extracted to the drive motor 34A.

For this reason, the attachment/detachment part 43 does not have a function to transmit a driving force, and even if the drive motor 34A is driven, the rotation of the output shaft 34a is not transmitted to the rotating shaft 32a. Therefore, the attachment/detachment part 43 is brought into the driving force release state.

For this reason, the attachment/detachment part 43 constitutes the driving force relay part capable of being switched between the driving force release state where a driving force is relayed and the driving force relay state where a driving force is cut off and the movement of the bending joint becomes free.

In this way, the present modification example is an example in a case where the driving force relay state and the driving force release state are realized by the attachment and detachment of the drive motor 34A.

Such a medical instrument 20A can be initialized by executing Steps S1 to S5 illustrated in FIG. 5, substantially similar to the manipulator system initialization method of the above first embodiment.

That is, the present modification example is different from the above first embodiment in that the medical instrument 20A is used instead of the medical instrument 20, and in Steps S1 and S3, the switching operation between the driving force relay state and the driving force release state is performed when the operator Op detaches and attaches the drive motor 34A from and to the fixing part 46.

Additionally, in Step S4 of the present modification example, the control unit 5A does not have the clutch control unit 102. Therefore, the present modification example is different from the above first embodiment in that the origin setting unit 101 is notified of being brought into the driving force release state by notification means (not illustrated) instead of the clutch control unit 102.

Such notification means may include, for example, means such as a detection sensor that detects a mounting state in conjunction with the attachment and detachment of the mounting member 45 or the drive motor 34, and means for manually performing notification with a pushbutton switch after an operator Op has finished mounting. The type of detection sensor may include, for example, instances of mechanical sensors, such as an optical sensor and a pushing switch, and detection sensors using an electrical field and a magnetic field.

In the present modification example, although illustration is omitted, a detection sensor interlocked with an operation in which the fitting projection 46a is pushed is provided, and the origin setting unit 101 is notified of being brought into the driving force relay state by the output of the detection sensor.

In the driving force release state of the present modification example, the drive motor 34A is detached from the drive unit 30A. Therefore, operating ability can be improved in that the weight of the medical instrument 20A can be reduced and an insertion operation into the treatment tool channel 16, and the like become easier.

(Second Embodiment)

Next, a manipulator system initialization method of a second embodiment of the invention will be described.

Figure 9:
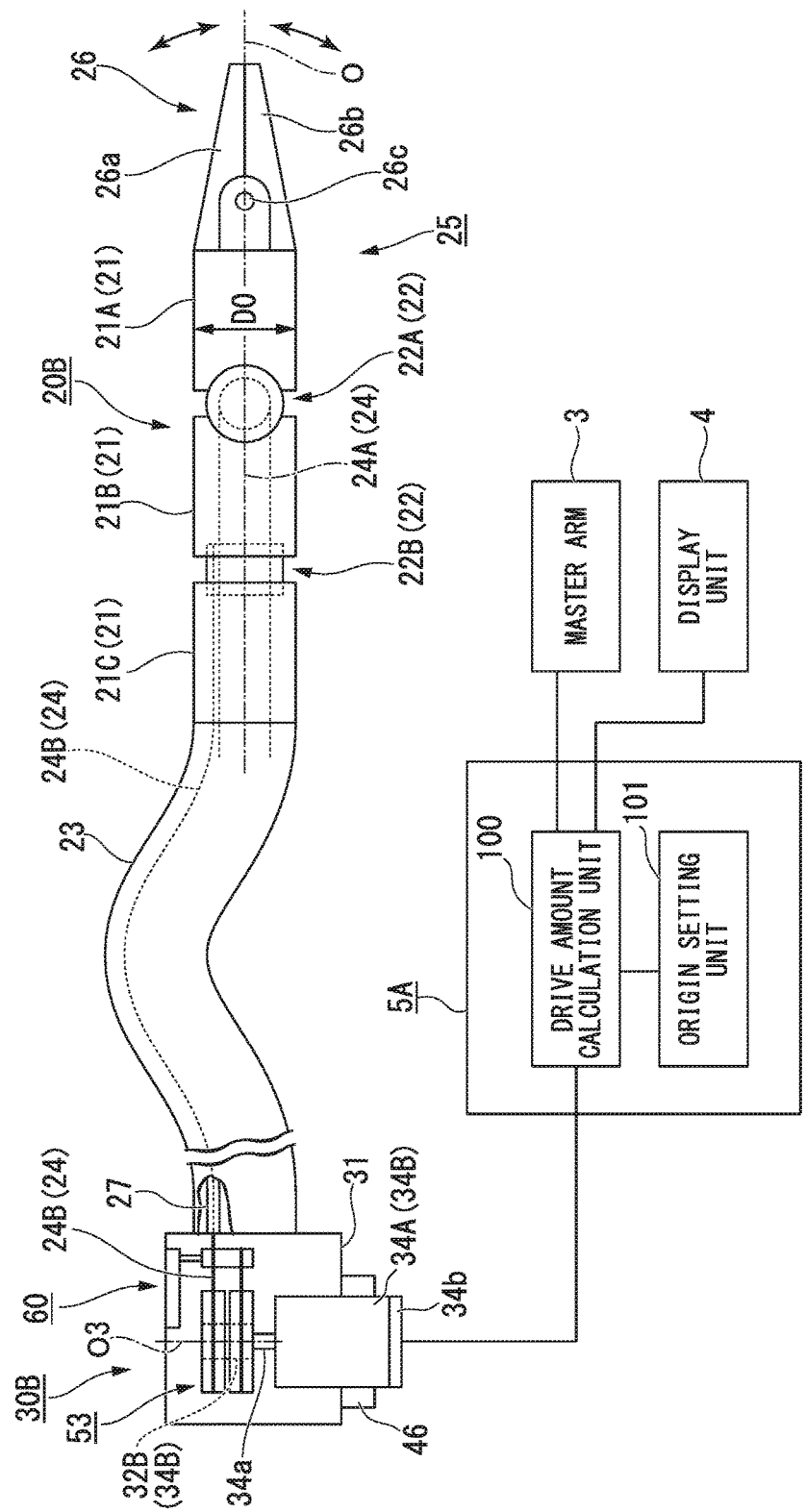
FIG. 9 is a schematic system configuration view of a medical instrument used for a manipulator system initialization method of a second embodiment of the invention.
Figure 10:
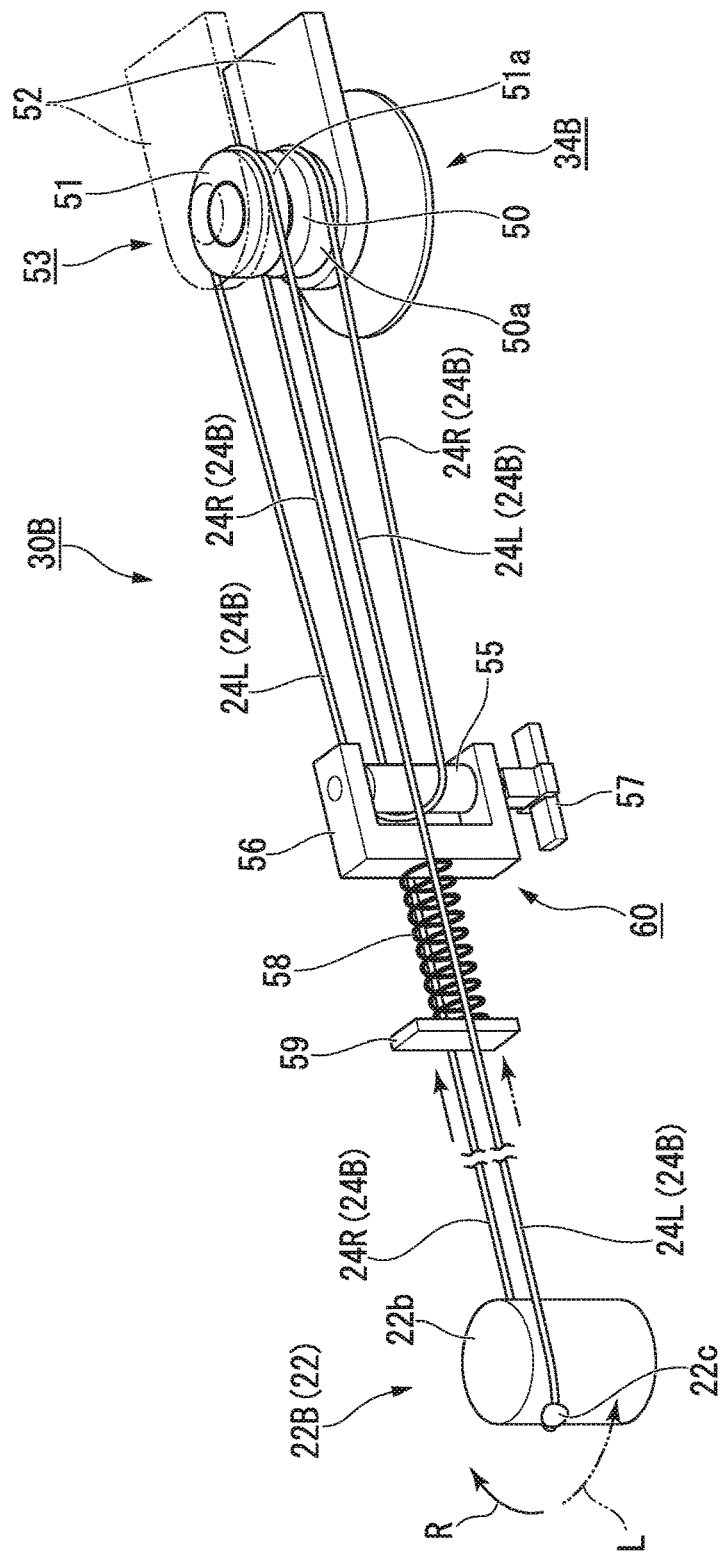
FIG. 10 is a schematic perspective view illustrating the configuration of an initial tension application part of the medical instrument used for the manipulator system initialization method of the second embodiment of the invention.
Figure 11:
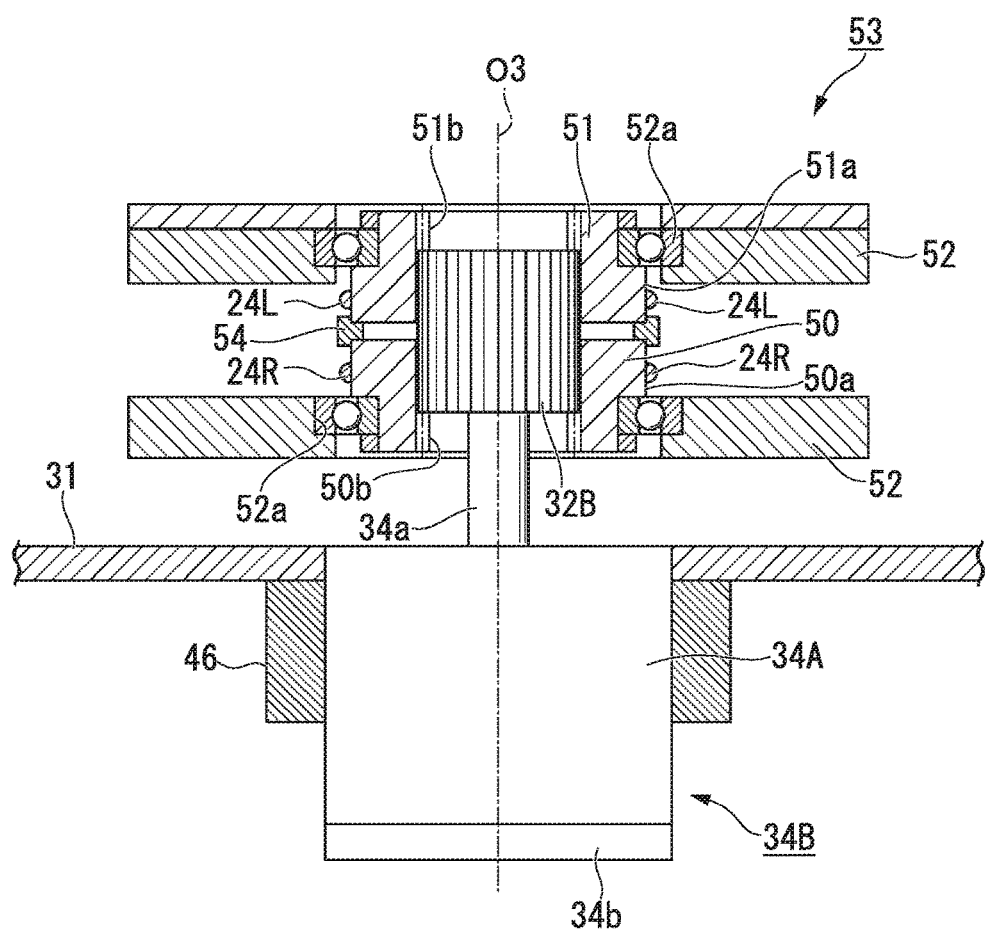
FIG. 11 is a schematic sectional view illustrating the configuration of a drive part and a driving force relay part of the medical instrument used for the manipulator system initialization method of the second embodiment of the invention.

FIG. 9 is a schematic system configuration view of a medical instrument used for the manipulator system initialization method of the second embodiment of the invention. FIG. 10 is a schematic perspective view illustrating the configuration of an initial tension application part of the medical instrument used for the manipulator system initialization method of the second embodiment of the invention. FIG. 11 is a schematic sectional view illustrating the configuration of a drive part and a driving force relay part of the medical instrument used for the manipulator system initialization method of the second embodiment of the invention.

Figure 12:
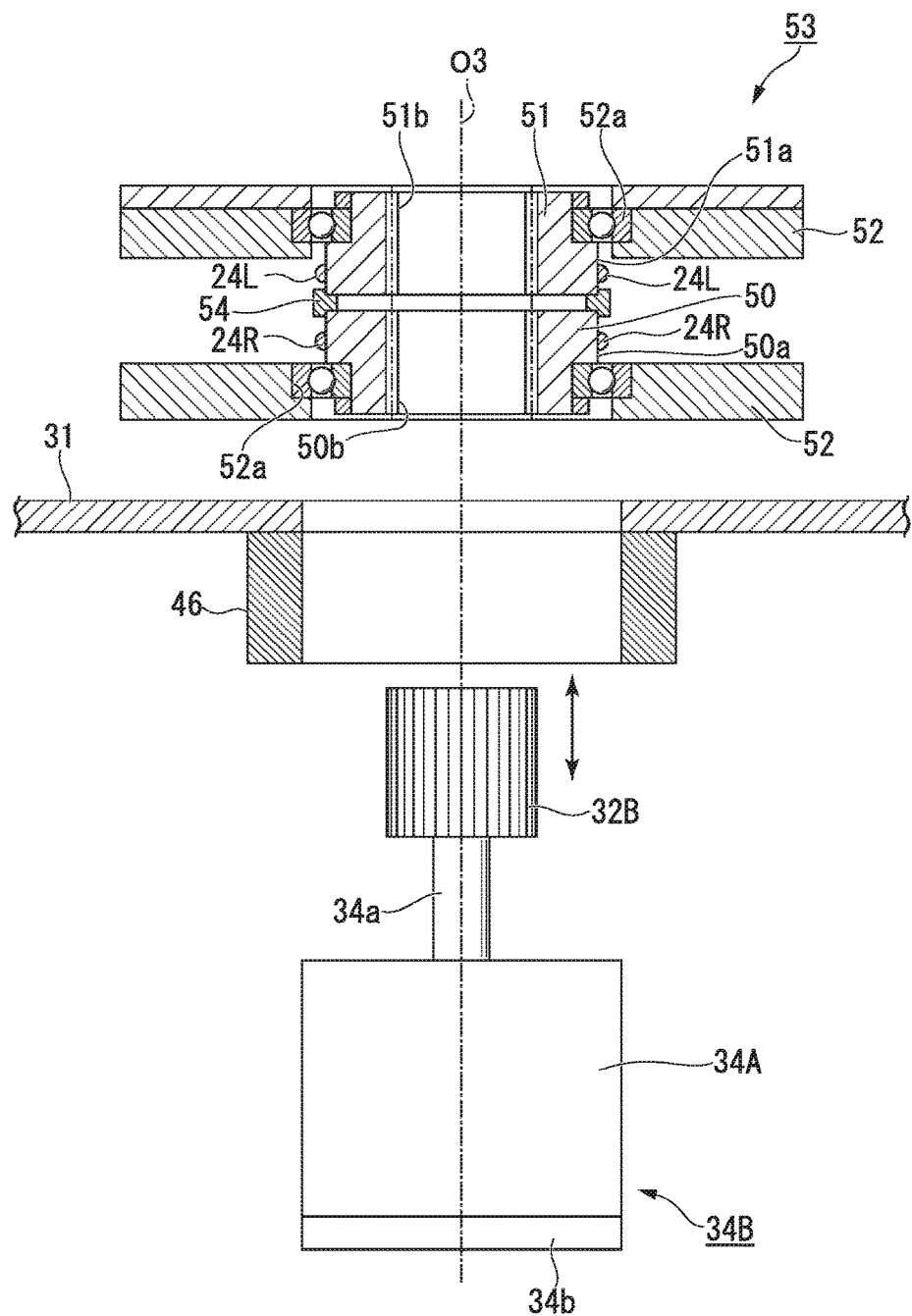
FIG. 12 is a schematic sectional view illustrating a driving force release state of the driving force relay part of the medical instrument used for the manipulator system initialization method of the second embodiment of the invention.

FIG. 12 is a schematic sectional view illustrating a driving force release state of the driving force relay part of the medical instrument used for the manipulator system initialization method of the second embodiment of the invention.

As illustrated in FIG. 1, a manipulator system 1B used for the manipulator system initialization method of the present embodiment includes a medical instrument 20B (manipulator) and the same control unit 5A (driving control unit) as that of the above first modification example, instead of the medical instrument 20 and the control unit 5 of the manipulator system 1 in the above first embodiment.

Hereinafter, differences from the above first embodiment will mainly be described.

As illustrated in FIG. 9, the medical instrument 20B includes a drive unit 30B, instead of the drive unit 30 of the medical instrument 20 of the above first embodiment.

The drive unit 30B includes a driving coupling part 53 (driving force relay part) and a drive motor part 34B, instead of the clutch 33, the drive pulley 32, and the drive motor 34 of the drive unit 30, and is obtained by adding the fixing part 46 that detachably fixes the drive motor part 34B to the housing of the driving mechanism part 31, and an initial tension application part 60.

In addition, although a set of the driving coupling part 53, the drive motor part 34B, the fixing part 46, and the initial tension application part 60 is provided according to each joint part 22, all of them have the same configuration. In the following, an example in a case where the joint part 22B is driven will be described.

As illustrated in FIG. 10, the driving coupling part 53 includes a first internal gear 50 and a second internal gear 51 around which the driving wire 24B is wound in order to pull the driving wire 24B.

The first internal gear 50 (second internal gear 51) has an outer peripheral surface 50a (51a) for allowing the driving wire 24B to be wound therearound, and is housed in a gear case 52 fixed to the housing of the driving mechanism part 31 (not illustrated).

In addition, in the present embodiment, an end part of the driving wire 24B is fixed at a position (not illustrated) on the outer peripheral surface 50a (51a) so that the rotation of the first internal gear 50 (second internal gear 51) is reliably transmitted to the driving wire 24B. Accordingly, it is possible to reliably pull the driving wire 24B without causing any slip or the like even in a case where large loosening has occurred in the driving wire 24B.

However, for example, in a case where no slip is caused only by frictional engagement, a configuration in which the driving wire is not fixed to the outer peripheral surface 50a (Ma) is also possible.

Both end parts of the driving wire 24B on the side of the joint part 22B are fixed to a pulley 22b in a junction part 22c after being wound around the pulley 22b of the joint part 22B.

An intermediate part of the driving wire 24B is wound around the outer peripheral surface 50a of the first internal gear 50 of the driving coupling part 53, a pulley 55 (to be described below) of the initial tension application part 60, and the outer peripheral surface Ma of the second internal gear 51 in this order.

In FIG. 10, which is a schematic view, the driving wire 24B is shown so as to be wound around the outer peripheral surfaces 50a, 51a and the pulley 55 by about a semiperimeter. However, the number of times of winding is not limited to about a semiperimeter. For example, an appropriate number of times of winding such as a semiperimeter or less or semiperimeter or more is possible.

Additionally, particularly, since the driving wire 24B is in frictional engagement with the pulley 55, it is preferable to wind the driving wire so that the winding angle of the driving wire becomes large so that the driving wire does not slip easily, and it is more preferable to wind the driving wire about 1 round or more.

In the following, with the location of the driving wires 24B wound around a central part of the pulley 55 as a center, a portion that faces the pulley 22b via the first internal gear 50 from the pulley 55 is referred to as a first wire part 24R, and a portion that faces the pulley 22b via the second internal gear 51 from the pulley 55 is referred to as a second wire part 24L.

As illustrated in FIG. 11, the first internal gear 50 and the second internal gear 51 are rotatably supported by a bearing 52a provided in the gear case 52, and a mutual positional relationship is fixed in an axially separated state by a washer 54. For this reason, the first internal gear 50 and the second internal gear 51 can be rotated in synchronization with each other, with a rotation center O3 as a center.

As the bearing 52a, for example, a ball bearing can be adopted.

Internal-teeth parts 50b and 51b which a pinion 32B of the drive motor part 34B (to be described below) is insertable into in the axial direction and is engageable with in the circumferential direction are formed coaxially with the rotation center axis O3 at central parts of the first internal gear 50 and the second internal gear 51.

The drive motor part 34B includes the drive motor 34A that generates a driving force for pulling the driving wire 24B, and the pinion 32B fixed to a distal end part of the output shaft 34a of the drive motor 34A coaxially with the output shaft 34a.

The drive motor 34A has the same configuration as that of the above first modification example except that the pinion 32B is fixed to the output shaft 34a, and the rotational operation thereof is controlled on the basis of a driving command value sent from the drive amount calculation unit 100 on the basis of an operation input using the master arm 3.

The pinion 32B is a gear that has a tooth form in which the pinion 32B meshes with the internal-teeth parts 50b and 51b of the first internal gear 50 and the second internal gear 51 at a position coaxial therewith. The face width of the pinion 32B is a face width such that the pinion 32B can mesh simultaneously with the internal-teeth parts 50b and 51b.

The drive motor part 34B with such a configuration, as illustrated in FIG. 9, is detachably fixed to the fixing part 46 provided in the housing of the driving mechanism part 31 in a positioned state in an outer peripheral part of the drive motor 34A. An attachment/detachment direction of the drive motor part 34B is a direction along the rotation center axis O3.

The fixing part 46 of the present embodiment has the same configuration as that of the fixing part 46 of the above first modification example except that the drive motor 34A is fixed, at a position where the pinion 32B meshes with the internal-teeth parts 50b and 51b by almost the same width (including the case of the same width) as the internal-teeth parts when fixing the drive motor 34A. Therefore, if the pinion 32B can be inserted at such a position, a configuration other than the example illustrated in FIGS. 8A and 8B is also possible, similar to the fixing part 46 of the above first modification example.

In FIG. 11, a state where the drive motor part 34B is mounted on the fixing part 46 is shown.

In contrast, in FIG. 12, a state where the drive motor part 34B is detached from the fixing part 46 is shown.

In the following descriptions, in a case where the positional relationship of the drive motor part 34B with respect to the driving coupling part 53 is described, a positional relationship in the mounting state of the drive motor part 34B will be described unless particularly mentioned.

Such a drive motor part 34B can be extracted and detached along the rotation center axis O3 as illustrated in FIG. 12 by releasing the fixation of the fixing part 46.

Additionally, the drive motor part 34B can be mounted on the fixing part 46 by being conversely pushed in along the rotation center axis O3. If the drive motor part 34B is mounted on the fixing part 46, the axial position of the drive motor part 34B is determined, and as illustrated in FIG. 11, the pinion 32B meshes with the internal-teeth parts 50b and 51b by almost the same width as the internal-teeth parts.

As illustrated in FIG. 10, the initial tension application part 60 includes the pulley 55 that has the intermediate part of the driving wire 24B wound around the outer peripheral surface thereof, a pulley holding part 56 that rotatably holds the pulley 55, a guide 57 that slidably holds the pulley holding part 56 in a direction in which a distal end (a left side in the illustration of FIG. 10) and a proximal end (a right side in the illustration of FIG. 10) in the drive unit 30B are connected together, a spring 58 disposed on the distal side of the pulley holding part 56 to pull the pulley holding part 56 toward the distal end side, and a support part 59 that supports a distal end of the spring 58.

The guide 57 and the support part 59 are fixed to the housing of the driving mechanism part 31 (not illustrated).

For this reason, the spring 58 pulls the pulley holding part 56 to the distal end side along the guide 57, and an initial tension corresponding to the elastic restoring force of the spring 58 is applied to the driving wire 24B. In this case, since the pulley holding part 56 is pulled by the spring 58 and is moved on a straight line, a configuration in which the guide 57 is eliminated is also possible.

However, the spring 58 may be arranged so as to press the pulley holding part 56 toward the distal end side. In this case, since there is a concern that the spring 58 may be buckled to the lateral side of an expansion/contraction direction thereof, the spring 58 may have a configuration that is different from the guide 57. However, it is preferable to provide a certain movement guide part that defines the movement direction of the pulley holding part 56.

The control unit 5A, as illustrated in FIG. 9, has the same configuration as that of the control unit 5A of the above first modification example, if controlling the driving of the drive motor 34A used for the drive motor part 34B of the present embodiment is excluded.

Next, the operation of the medical instrument 20B in the manipulator system 1B will be described.

Figure 13A:
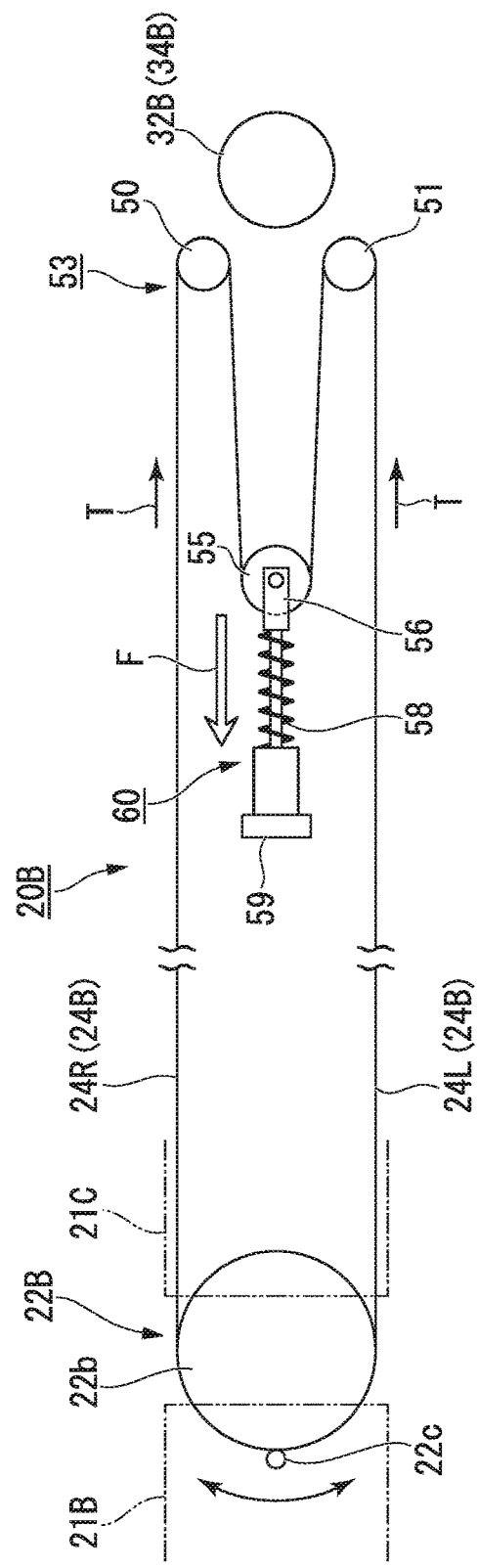
FIG. 13A is a schematic operation explanatory view of principal parts of the medical instrument used for the manipulator system initialization method of the second embodiment of the invention.
Figure 13B:
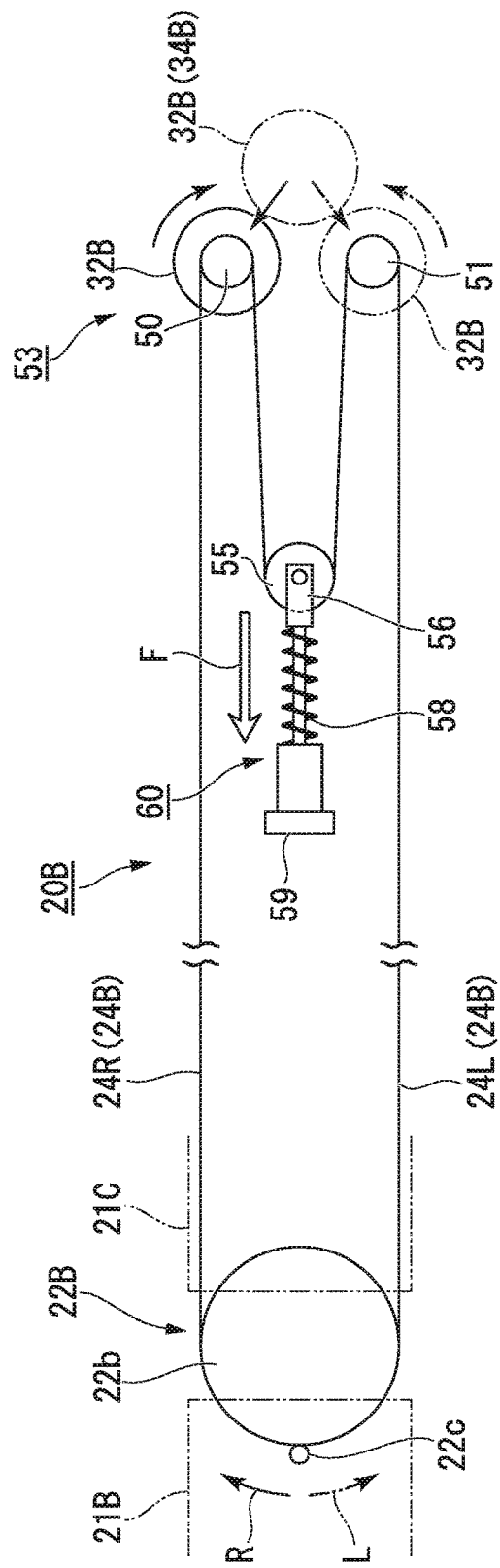
FIG. 13B is a schematic operation explanatory view of principal parts of the medical instrument used for the manipulator system initialization method of the second embodiment of the invention.

FIGS. 13A and 13B are schematic operation explanatory views of principal parts of the medical instrument used for the manipulator system initialization method of the second embodiment of the invention.

The drive motor part 34B of the medical instrument 20B is detachably fixed to the housing of the driving mechanism part 31 via the fixing part 46.

Main components that drive the joint part 22B in the medical instrument 20B are schematically illustrated in FIGS. 13A and 13B. Since the wiring of the driving wire 24B is deployed and expressed on a plane for simplicity, the positions of the first internal gear 50 and the second internal gear 51 are shown so as to be shifted from each other. FIG. 13A illustrates a detachment state of the drive motor part 34B, and FIG. 13B illustrates a mounting state of the drive motor part 34B.

As illustrated in FIG. 12, if the drive motor part 34B is detached from the driving coupling part 53, the pinion 32B does not mesh with the first internal gear 50 and the second internal gear 51. Therefore, even if the drive motor 34A is driven, a driving force is not transmitted to the first internal gear 50 and the second internal gear 51, and the driving wire 24B is not pulled.

In this case, as illustrated in FIG. 13A, the driving wire 24B is sequentially wound around the pulley 22b of the joint part 22B, the first internal gear 50, the pulley 55 of the initial tension application part 60, and the second internal gear 51. Additionally, the driving wire 24B is fixed on the outer peripheral surfaces of the first internal gear 50 and the second internal gear 51 at positions that are not illustrated and is fixed to pulley 22b via the junction part 22c on the pulley 22b to form a loop.

In addition, FIGS. 13A and 13B are schematic views, which are simplified. For this reason, the wiring, the winding angle, the number of times of winding, and the like in the driving wire 24B are not precisely expressed.

The pulley 55 is pulled to the distal end side with a force F by the spring 58. For this reason, in each of the first wire part 24R and the second wire part 24L divided with the pulley 55 as a border, an initial tension T (=F/2) is applied to the driving wire 24B.

Accordingly, the driving wire 24B is stretched without causing loosening.

In this state, for example, if an external force to rotate the joint part 22B acts on the shaft-shaped part 21B, the pulley 22b rotates because the pulley 22b, the first internal gear 50, the pulley 55, and the second internal gear 51 are all smoothly and rotatably held. Additionally, in conjunction with this, the first internal gear 50, the pulley 55, and the second internal gear 51 also rotate according to the movement distance of the driving wire 24B. Thus, the joint angle varies freely within the movable range.

Therefore, the driving coupling part 53 is brought into the driving force release state where the movement of the joint part 22B becomes free.

For example, as illustrated in FIG. 11, if the drive motor part 34B is mounted on the driving coupling part 53, the pinion 32B meshes with the internal-teeth parts 50b and 51b of the first internal gear 50 and the second internal gear 51. For this reason, it is possible to transmit a driving force from the pinion 32B to the first internal gear 50 and the second internal gear 51.

That is, if a driving command value is sent from the drive amount calculation unit 100 of the control unit 5A, the drive motor 34A is driven, the pinion 32B rotates, and a driving force is transmitted to the first internal gear 50 and the second internal gear 51.

In this way, the driving coupling part 53 of the present embodiment constitutes the driving force relay part capable of being switched between the driving force release state where a driving force is relayed and the driving force relay state where a driving force is cut off and the movement of the bending joint becomes free.

In this way, the present embodiment is an example in a case where the driving force relay state and the driving force release state are realized by the attachment and detachment of the drive motor part 34B.

Such a medical instrument 20B can be initialized, substantially similar to the manipulator system initialization method of the above first embodiment.

Specifically, Steps S11 to S16 illustrated in FIG. 14 are executed according to the flow illustrated in FIG. 14.

FIG. 14 is a flowchart illustrating the flow of the manipulator system initialization method of the second embodiment of the invention.

First, Step S11 is performed. This step is a step of applying an initial tension to each driving wire 24 in order to bring the drive motor part 34B into the detachment state, thereby bringing the driving coupling part 53 that is the driving force relay part into the driving force release state to remove the loosening of each driving wire 24.

When the medical instrument 20B has the initial tension application part 60, the initial tension is always applied. For this reason, this step is not a step where the operator Op and the control unit 5A need to perform particularly a certain operation.

However, since there is a concern that the initial tension may not be applied if the initial tension application part 60 fails, it is preferable to proceed to the following step after being confirmed that the initial tension application part 60 is normally operating.

Step S11 constitutes an initial tension applying step of applying an initial tension to a driving force transmission member in order to remove loosening of the driving force transmission member.

Steps S12 to S16 are almost the same steps as Steps S1 to S5 (refer to FIG. 5) of the above first embodiment.

That is, Steps S12 to S16 are different from the above first embodiment in that the medical instrument 20B is used instead of the medical instrument 20, and in Step S14, the switching operation of performing switching to the driving force relay state is performed when the operator Op mounts the drive motor part 34B to the fixing part 46, unlike the above Step S3.

In the present embodiment, since the medical instrument 20B is brought into the driving force release state in Step S11, it is not necessary to perform particularly the operation of bringing the medical instrument into the driving force release state in Step S12.

Additionally, since the driving wire 24 is brought into a state where the loosening thereof is removed after the execution of Step S11, the driving wire 24 is in a state where the loosening thereof is removed even when being brought into the driving force relay state in Step S14.

According to the initialization method of the present embodiment, since almost the same Steps S12 to S15 as those of the above first embodiment are performed, the joint angle of the bending joints can be precisely initialized. Additionally, the drive limit is set by performing Step S16 and thus the distal end bending part 25 is not excessively bent. Therefore, an excessive load can be prevented from being applied to the medical instrument 20B or a medical treatment target.

Moreover, in Step S11, the loosening is removed by applying the initial tension to each driving wire 24. Therefore, the loosening is removed even if the path length of the driving wire 24 varies when the medical instrument 20B is bent along the treatment tool channel 16 after Step S12.

For this reason, since the loosening is removed even when being brought into the driving force relay state in Step S14, a driving error caused by the loosening of the driving wire 24 can be eliminated. Accordingly, a more precise bending operation can be performed.

(Second Modification Example)

Next, a manipulator system initialization method of a modification example (second modification example) of the above second embodiment will be described.

In the above second embodiment, an example in a case where the initial tension applying step is first performed has been described. However, applying the initial tension to remove the loosening of the driving wire 24 is performed in order to reduce the setting error of the drive origin.

For this reason, the initial tension applying step may be executed any time as long as the timing to execute the initial tension applying step is before Step S15 that is the origin setting step.

For this reason, Step S11 of the above second embodiment can be modified so as to be executed at any one timing of between Step S12 and S13, between Step S13 and S14, and between Step S14 and S15.

However, since the loosening of the driving wire 24 can be easily removed in the driving force release state, it is more preferable to execute before Step S14 that is the drive part coupling step.

In order to execute the initial tension applying step, specifically, a switch that is switched between a state where the spring 58 pulls the pulley holding part 56 and a state where the biasing force of the spring 58 is released may be provided.

(Third Embodiment)

Next, a manipulator system initialization method of a third embodiment of the invention will be described.

Figure 15:
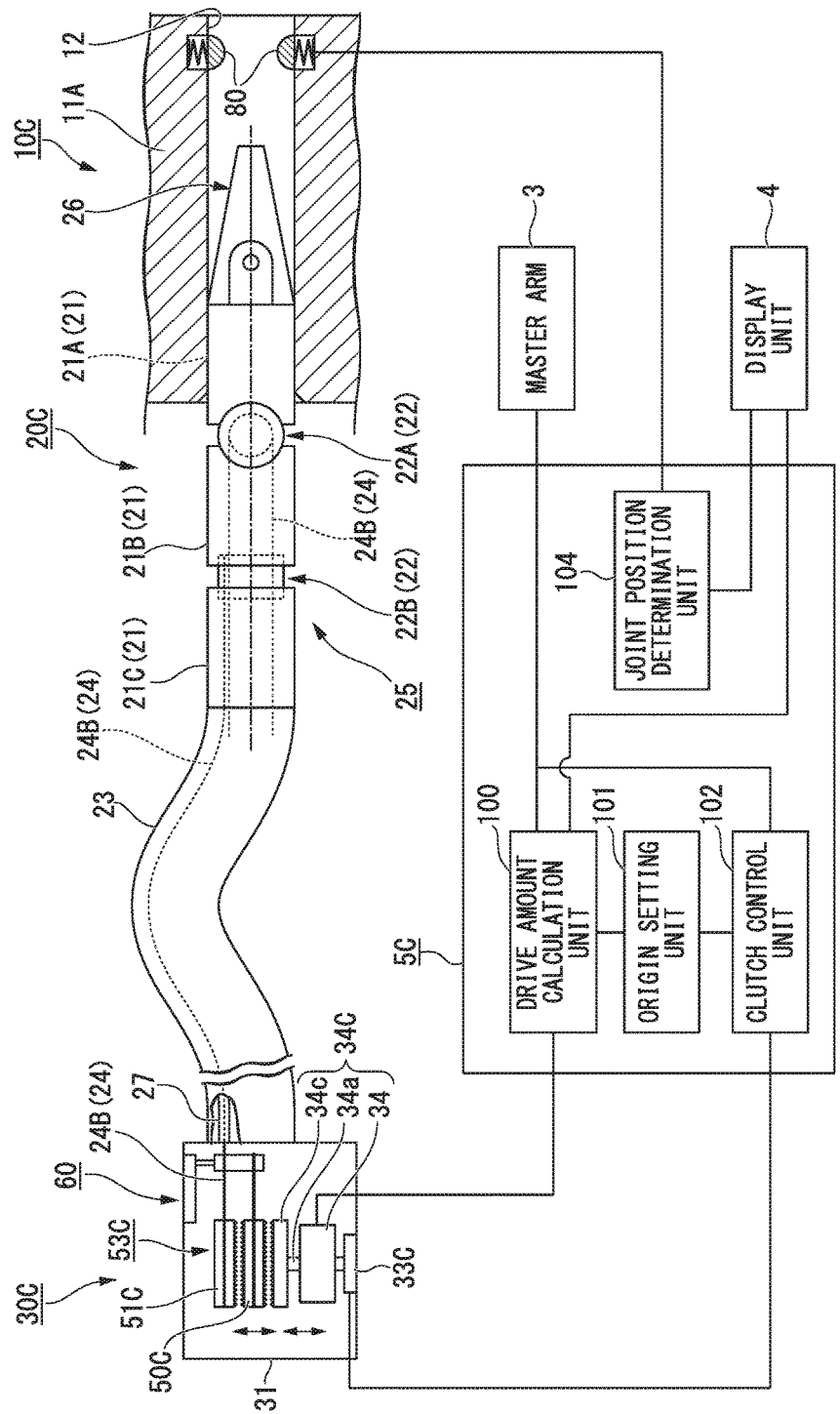
FIG. 15 is a schematic system configuration view of a medical instrument and a shape defining member used for a manipulator system initialization method of a third embodiment of the invention.
Figure 16A:
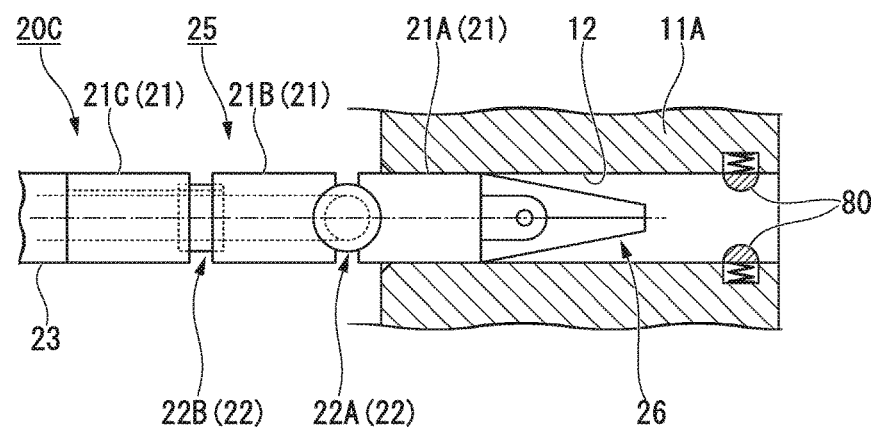
FIG. 16A is a schematic sectional view illustrating the relationship between the position of a joint position detection unit of an endoscope apparatus for treatment and an insertion position of the medical instrument that are used for the manipulator system initialization method of the third embodiment of the invention.
Figure 16B:
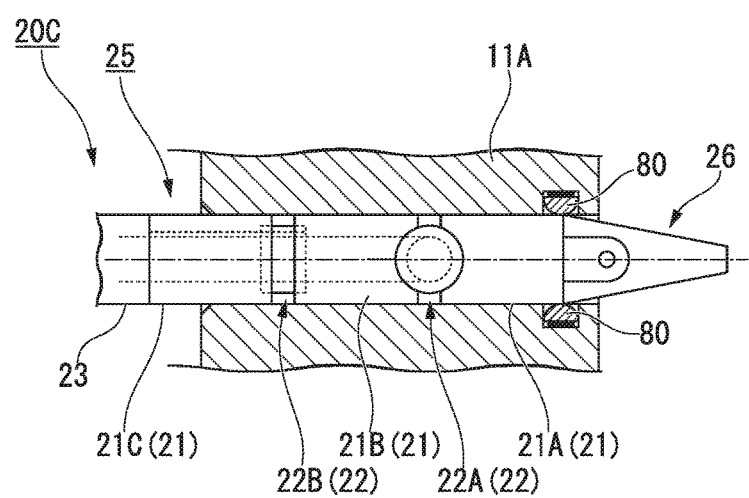
FIG. 16B is a schematic sectional view illustrating the relationship between the position of the joint position detection unit of the endoscope apparatus for treatment and the insertion position of the medical instrument that are used for the manipulator system initialization method of the third embodiment of the invention.

FIG. 15 is a schematic system configuration view of a medical instrument and a shape defining member used for the manipulator system initialization method of the third embodiment of the invention. FIGS. 16A and 16B are schematic sectional views illustrating the relationship between the position of a joint position detection unit of an endoscope apparatus for treatment and an insertion position of the medical instrument that are used for the manipulator system initialization method of the third embodiment of the invention.

As illustrated in FIG. 1, a manipulator system 1C used for the manipulator system initialization method of the present embodiment includes a medical instrument 20C (manipulator), an endoscope apparatus 10C for treatment, and a control unit 5C (driving control unit), instead of the medical instrument 20, the endoscope apparatus 10 for treatment, and the control unit 5 of the manipulator system 1 in the above first embodiment.

Hereinafter, differences from the above first embodiment will mainly be described.

As illustrated in FIG. 15, the medical instrument 20C includes a drive unit 30C, instead of the drive unit 30B of the medical instrument 20B of the above second embodiment.

The drive unit 30C includes a driving coupling part 53C and the drive motor part 34C, instead of the driving coupling part 53 and the drive motor part 34B of the above second embodiment, and is obtained by adding a clutch 33C.

In addition, although a set of the driving coupling part 53C, the drive motor part 34C, the clutch 33C, and the initial tension application part 60 is provided for each joint part 22, all of them have the same configuration. In the following, an example in a case where the joint part 22B is driven will be described.

The driving coupling part 53C includes a first pulley 50C and a second pulley 51C, instead of the first internal gear 50 and the second internal gear 51 of the above second embodiment.

The first pulley 50C and the second pulley 51C are rotatably supported similar to the first internal gear 50 and the second internal gear 51, respectively, with the internal-teeth parts 50b and 51b of the first internal gear 50 and the second internal gear 51 of the above second embodiment being eliminated therefrom. However, in the present embodiment, the first pulley 50C is supported so as to be capable of being brought into contact with and separated from the second pulley 51C in a direction (a double-headed direction in the drawing, hereinafter, referred to as a rotational axis direction) along a rotational axis by a movable support member (not illustrated).

That is, the movable support member is supported at a position where the first pulley 50C is separated from the second pulley 51C in a state where an external force equal to or more than a fixed value that presses the first pulley 50C in the rotational axis direction does not act on the first pulley 50C. If the external force equal to more than the fixed value acts on the first pulley 50C, the first pulley 50C moves in the rotational axis direction and abuts against the second pulley 51C.

Abutting surfaces between the first pulley 50C and the second pulley 51C are formed as engagement surfaces (not illustrated) including a concavo-convex shape, and thereby, the first pulley and the second pulley are rotatable integrally with each other at the time of abutment.

Additionally, the first pulley 50C also has the same engagement surface on a rear surface side thereof.

The drive motor part 34C is obtained by providing the output shaft 34a of the drive motor 34 of the above first embodiment with an engagement plate 34c that is capable of being brought into contact with and separated from the engagement surface of the first pulley 50C opposite to the second pulley 51C in the rotational axis direction.

The engagement plate 34c transmits the rotational driving force from the output shaft 34a, to the first pulley 50C when the engagement plate abuts against the engagement surface of the first pulley 50C at an opposed position thereof.

The drive motor part 34C is supported so as to be advanceable and retractable in the rotational axis direction by the movable support member (not illustrated).

The clutch 33C is a device part that advances and retracts the drive motor part 34C in a direction along the output shaft 34a, according to a control signal from the clutch control unit 102, and is fixed between an end part of the drive motor part 34C opposite to the output shaft 34a, and the housing of the driving mechanism part 31.

If a control signal for advancing the drive motor part 34C is transmitted to the clutch 33C, the drive motor part 34C moves in the direction along the output shaft 34a toward the first pulley 50C.

Accordingly, the engagement plate 34c is pressed against the engagement surface of the first pulley 50C with a force equal to or more than the fixed value, the opposite engagement surface of the first pulley 50C abuts against the engagement surface of the second pulley 51C, and the engagement plate 34c, the first pulley 50C, and the second pulley 51C are coupled together.

For this reason, if the output shaft 34a rotates, the driving force from the drive motor part 34C is relayed, and the first pulley 50C and the second pulley 51C rotate synchronously. That is, the driving force relay state is formed.

If a control signal for retracting the drive motor part 34C is transmitted to the clutch 33C, the drive motor part 34C moves in a direction away from the first pulley 50C.

Accordingly, the engagement plate 34*c*, the first pulley 50C, and the second pulley 51C are separated from each other, and the driving force release state where a driving force is cut off is formed.

For this reason, the clutch 33C is the driving force relay part that is switched between the driving force relay state and the driving force release state.

The endoscope apparatus 10C for treatment is different from the endoscope apparatus 10 for treatment in that a joint position detection unit 80 is provided at a fixed position within the shape defining part 12 of the above first endoscope apparatus 10 for treatment.

The joint position detection unit 80 is not particularly limited if the insertion state of the joint part 22 and the shaft-shaped parts 21 with respect to the shape defining part 12 can be detected, and thereby, whether or not the setting of the joint angle of the joint part 22 succeeds can be confirmed by the shape defining part 12.

In the present embodiment, similar to the above first embodiment, the joint angle is set to a predetermined value when the joint part 22 that defines the joint angle, and the pair of shaft-shaped parts 21 coupled to the joint part are inserted into the shape defining part 12.

Therefore, all means that can perform detection on whether or not a specific joint part 22 is located in the shape defining part 12 together with the shaft-shaped parts 21 coupled to the joint part can be used for the joint position detection unit 80.

In the present embodiment, a push-in switch type position sensor that protrudes further to a radial inner side than a fitting gap between each shaft-shaped part 21 and the shape defining part 12 and is switched on if the shaft-shaped part 21 is inserted is adopted as an example of the joint position detection unit 80.

Such a joint position detection unit 80 generates a detection signal, for example, when a distal end of the shaft-shaped part 21A passes therethrough, if the distal end bending part 25 is inserted as illustrated in FIG. 16A.

In this case, as illustrated in FIG. 16B, if the shaft-shaped part 21C is in a positional relationship where this shaft-shaped part is inserted into the shape defining part 12 by a fixed length or more, the shaft-shaped part 21A, the joint part 22A, the shaft-shaped part 21B, and the joint part 22B are altogether inserted into the shape defining part 12. Therefore, if the joint position detection unit 80 is installed at such a position, it can be determined whether or not the setting of the joint angle of the joint parts 22A and 22B succeeds.

Although a case where joint position detection units 80 are provided in two places that face each other in the radial direction is illustrated in FIGS. 16A and 16B, this is an example. As for the number and the arrangement position of the joint position detection unit 80, a configuration in which a suitable number of joint position detection units are arranged can be adopted if necessary.

For example, the passage situation and the insertion length of a distal end part of the shaft-shaped part 21A of the distal end bending part 25 can be determined by providing a plurality of joint position detection units 80 along the axial direction in the shape defining part 12.

For example, as for the position of the shaft-shaped part 21A, by arranging the joint position detection units 80 within allowable ranges, it is also possible to determine that the amount of insertion is excessive and the setting of the joint angle has failed.

The control unit 5C, as illustrated in FIG. 15, is obtained by adding a joint position determination unit 104 to the control unit 5 of the above first embodiment.

The joint position determination unit 104 is communicably connected to the joint position detection unit 80 provided in the endoscope apparatus 10C for treatment, and determines the position, in the shape defining part 12, of each joint part 22 inserted into the shape defining part 12, on the basis of a detection signal of the joint position detection unit 80.

The joint position determination unit 104 is communicably connected to the display unit 4, and causes the position of the joint part 22 determined on the basis of the detection signal of the joint position detection unit 80, or information on whether or not the setting of the joint angle has succeeded to be displayed on the display unit 4. In the following, information displayed in a case where the setting of the joint angle has succeeded is referred to as success information, and information displayed in a case where the setting of the joint angle has failed is referred to as failure information.

In a case where the position of the joint part 22 is displayed with a numerical value or a graph, the operator Op can view the numerical value or a graph to determine success or failure.

Next, the manipulator system initialization method of the present embodiment of the invention using the medical instrument 20C will be described.

Figure 17:
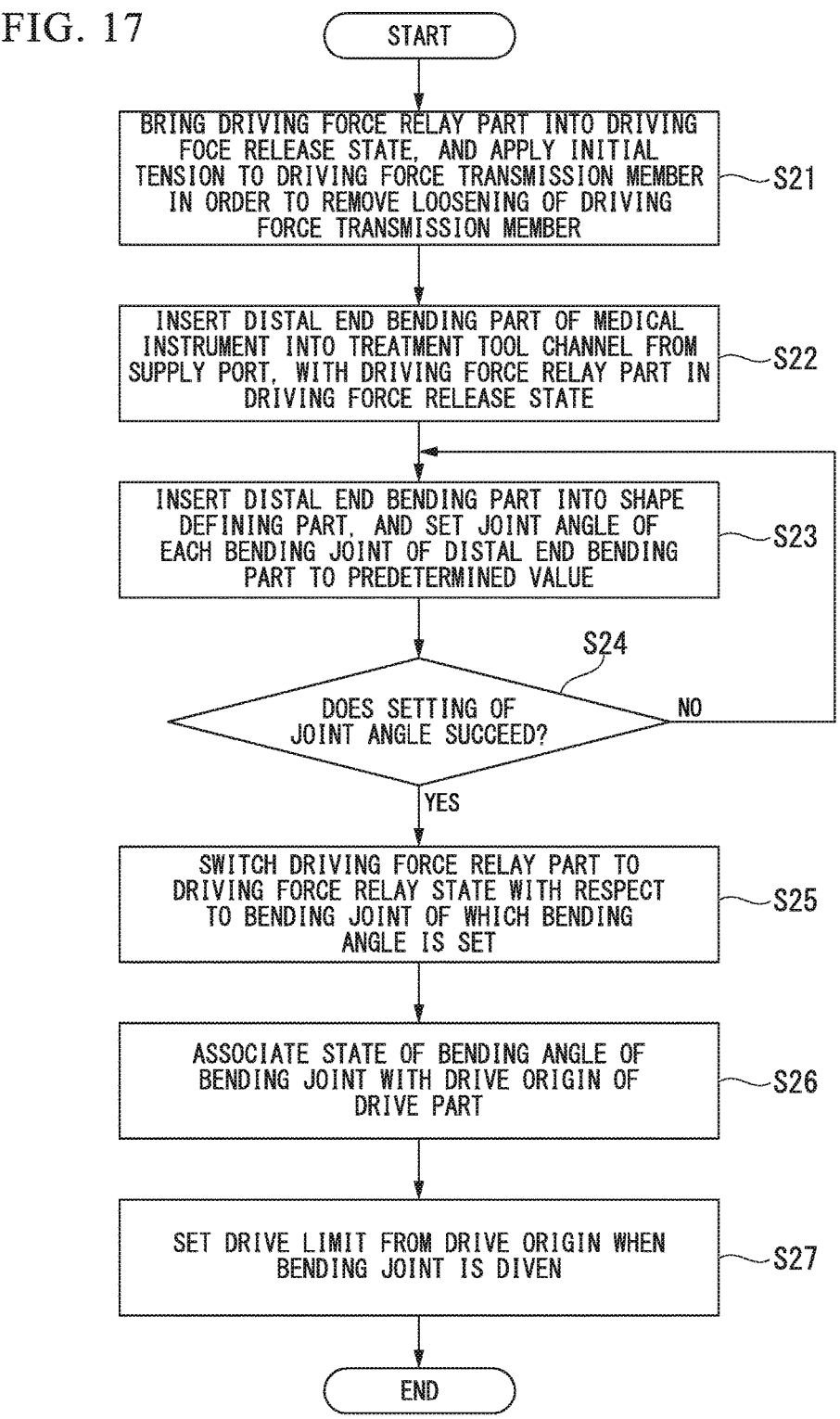
FIG. 17 is a flowchart illustrating the flow of the manipulator system initialization method of the third embodiment of the invention.

FIG. 17 is a flowchart illustrating the flow of a manipulator system initialization method of a third embodiment of the invention.

The manipulator system initialization method of the present embodiment is a method of executing Steps S21 to S27 illustrated in FIG. 17 according to the flow of FIG. 17.

Steps S21 to S23 are the same steps as Steps S11 to S13 (refer to FIG. 14) in the above second embodiment, except for being performed using the medical instrument 20C.

However, in Step S23 of the present embodiment, the operator Op proceeds to Step S24 if the medical instrument 20C is pushed in by an appropriate amount.

Step S24 is a step of determining whether or not the setting of the joint angle of the joint part 22 succeeds, on the basis of the detection signal of the joint position detection unit 80, and constitutes an insertion state determining step of the present embodiment.

In the present embodiment, the joint position determination unit 104 monitors the detection signal of the joint position detection unit 80

In the present embodiment, the joint position determination unit 104 causes the display unit 4 to display the success information in the setting of each joint part 22 if the detection signal is received from the joint position detection unit 80.

For this reason, the operator Op can view the display of the display unit 4 to know the determination result obtained by the joint position determination unit 104.

When the operator Op confirms that the success information has been displayed on the display unit 4, the insertion of the medical instrument 20C is ended, and the processing proceeds to Step S25.

If the success information is not displayed on the display unit 4, the processing proceeds to Step S23.

That is, the operator Op further inserts the medical instrument 20C toward the distal end. However, in a case where the joint position determination unit 104 has found that excessive insertion has been made, for example, by the failure information, the insertion position, or the like being displayed, the operation of returning the medical instrument 20C to the base end side and resuming insertion is also possible in Step S23.

Steps S25 to S27 are almost the same steps as Steps S14 to S16 (refer to FIG. 14) in the above second embodiment, except for being performed using the medical instrument 20C.

However, in the above second embodiment, in Step S14, switching to the driving force relay state is performed in a state where the drive motor part 34B is mounted. In contrast, in Step S25 of the present embodiment, there is a difference in that the clutch 33 is operated and switched to the driving force relay state, similar to Step S3 of the above first embodiment.

From above, each joint part 22 of the medical instrument 20C is initialized.

According to the initialization method of the present embodiment, the joint angle of the bending joint can be precisely initialized similar to the above first and second embodiments. Additionally, an excessive load can be prevented from being applied to the medical instrument 20C or a medical treatment target. Additionally, a driving error caused by the loosening of the driving wire 24 can be eliminated. Accordingly, a more precise bending operation can be performed.

(Third to Fifth Modification Examples)

Next, manipulator system initialization methods of modification examples (third to fifth modification examples) of the above third embodiment will be described.

Figure 18A:
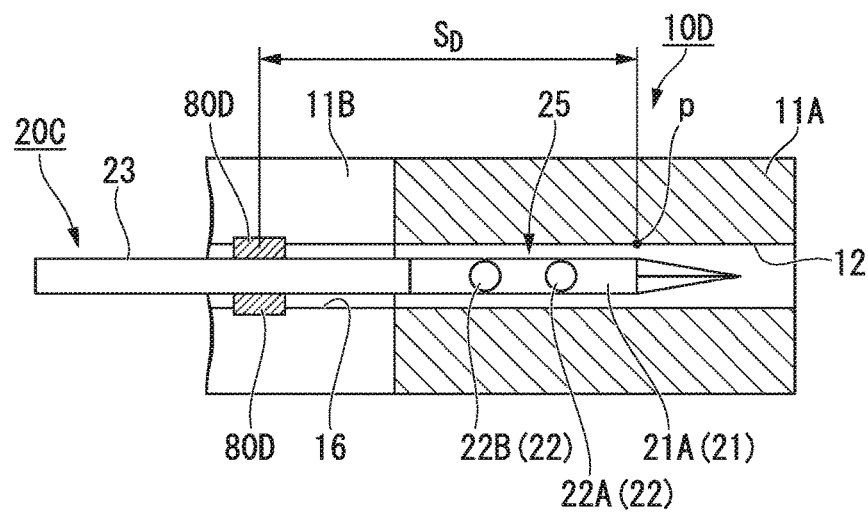
FIG. 18A is a schematic sectional view illustrating an example of a joint position detection unit used for a manipulator system initialization method of a third modification example of the third embodiment of the invention.
Figure 18B:
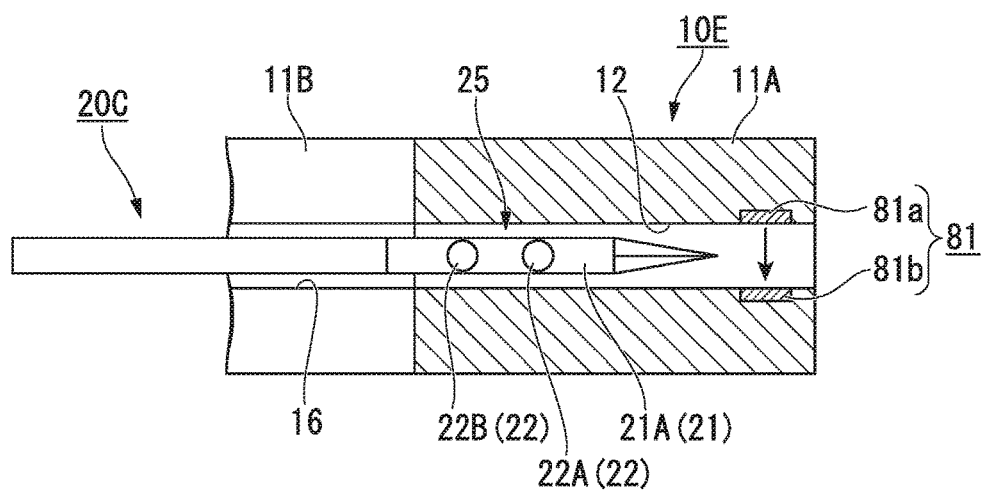
FIG. 18B is a schematic sectional view illustrating an example of a joint position detection unit used for a manipulator system initialization method of a fourth modification example of the third embodiment of the invention.
Figure 18C:
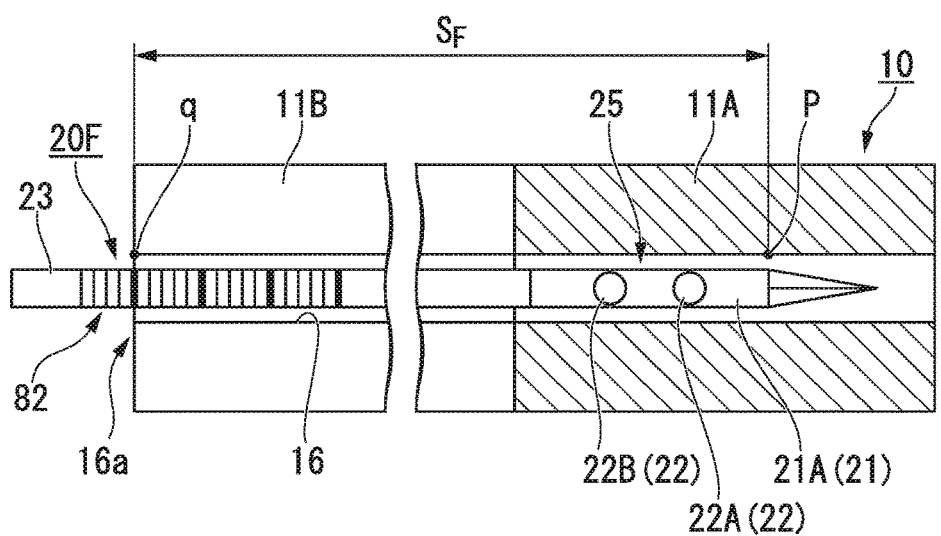
FIG. 18C is a schematic sectional view illustrating an example of a joint position detection unit used for a manipulator system initialization method of a fifth modification example of the third embodiment of the invention.

FIGS. 18A, 18B, and 18C are schematic sectional views illustrating an example of a joint position detection unit used for the manipulator system initialization methods of modification examples (third to fifth modification examples) of the third embodiment of the invention.

The third modification example illustrated in FIG. 18A is a modification example using an endoscope apparatus 10D for treatment, instead of the endoscope apparatus 10C for treatment in the above third embodiment.

The endoscope apparatus 10D for treatment includes a joint position detection unit 80D that is arranged at a specific position on an inner peripheral part of the treatment tool channel 16, and detects reaching of each shaft-shaped part 21 at the position, instead of the joint position detection unit 80 of the endoscope apparatus 10C for treatment.

For example, a push-in switch type position sensor that protrudes further to the radial inner side than a fitting gap between the shaft-shaped part 21 and the treatment tool channel 16 and is switched on if the shaft-shaped part 21 is inserted is adopted as the joint position detection unit 80D.

That is, the present modification example is an example in a case where the same sensor is arranged in a part other than the shape defining part 12, whereas the endoscope apparatus 10C for treatment of the above third embodiment is configured such that the joint position detection unit 80 is arranged in the shape defining part 12.

According to the joint position detection unit 80D of the present modification example, it is possible to detect that the distal end of the shaft-shaped part 21A has reached the specific position of the treatment tool channel 16. For example, the arrangement position of the joint position detection unit 80 is a position with a length SD toward the proximal end side from a position p within the shape defining part 12 that the shaft-shaped part 21A should reach. In this case, the operator Op can see that the setting of the joint angle succeeds if the medical instrument 20C is inserted by a length S from a position where the detection signal from the joint position detection unit 80 is generated. Accordingly, the above Steps S23 and S24 are executed.

Additionally, in the case of the present modification example, the joint position detection unit 80D may detect a projection or a marker that is provided at an appropriate position on the tubular part 23. In this case, if a detection signal is generated corresponding to such a projection or a marker, the distal end of the shaft-shaped part 21A is located at the position p at that time. Therefore, it can be seen that the setting of the joint angle succeeds.

The fourth modification example illustrated in FIG. 18B is a modification example using an endoscope apparatus 10E for treatment, instead of the endoscope apparatus 10C for treatment in the above third embodiment.

The endoscope apparatus 10D for treatment includes the joint position detection unit 81 consisting of an optical sensor, instead of the joint position detection unit 80 of the endoscope apparatus 10C for treatment.

The joint position detection unit 81 consists of a light emitting part 81a that emits detection light, and a light-receiving part 81b that photoelectrically converts the detection light and generates a detection signal according to the quantity of light received.

The light emitting part 81a and the light-receiving part 81b are arranged at mutually corresponding positions in the vicinity of an inner peripheral surface of the shape defining part 12.

According to such a joint position detection unit 81, it is possible to detect that the distal end bending part 25 is advanced to a position where the detection light is cut off. Accordingly, the above Steps S23 and S24 are executed.

According to the joint position detection unit 81, since the position of the distal end bending part 25 can be detected in a contactless manner, it is possible to advance and retract the distal end bending part 25 more smoothly than the contact type joint position detection unit 80.

Additionally, in a case where the optical sensor is used, the configuration of a reflective optical sensor in which the light emitting part 81a and the light-receiving part 81b are arranged adjacent to each other in the axial direction of the shape defining part 12, and the detection light reflected by the surface of the distal end bending part 25 in the detection light from the light emitting part 81a is received by the light-receiving part 81b is also possible. In this case, by providing a marker having a reflecting surface on the surface of the distal end bending part 25, it is possible to detect that a marker has reached this surface.

The fifth modification example illustrated in FIG. 18C is a modification example using a medical instrument 20F, instead of the medical instrument 20C in the above third embodiment.

The medical instrument 20F is an example in which an insertion amount detection marker 82 (joint position detection unit) is provided as the joint position detection unit on the surface of the tubular part 23 of the medical instrument 20C on the proximal end side. In the case of the present modification example, sensors, such as the joint position detection unit 80, are not required for the overtube 11 side. Therefore, the endoscope apparatus 10C for treatment can be replaced with the endoscope apparatus 10 for treatment of the above first embodiment.

As the insertion amount detection marker 82, for example, number lines with which the amount of insertion can be read by viewing or by an optical reading sensor, a magnetic sensor, or the like that is not illustrated, or markers, such as graduations, can be adopted.

In the present modification example, in order to reliably set the joint angle, a length SF from the supply port 16a of the overtube 11 to a position equivalent to the position p of the distal end part 11A, and the position q of the insertion amount detection marker 82 with a length SF from the distal end of each shaft-shaped part 21 on the medical instrument 20F are obtained in advance.

For this reason, when the insertion amount detection marker 82 indicating the position q reaches the supply port 16a, it can be seen that the setting of the joint angle has succeeded.

Thus, the operator Op inserts the medical instrument 20F while monitoring the insertion amount detection marker 82 in the supply port 16a, and stops the insertion if the position q is reached in the supply port 16a. Accordingly, the above Steps S23 and S24 are executed.

(Fourth Embodiment)

Next, a manipulator system initialization method of a fourth embodiment of the invention will be described.

Figure 19A:
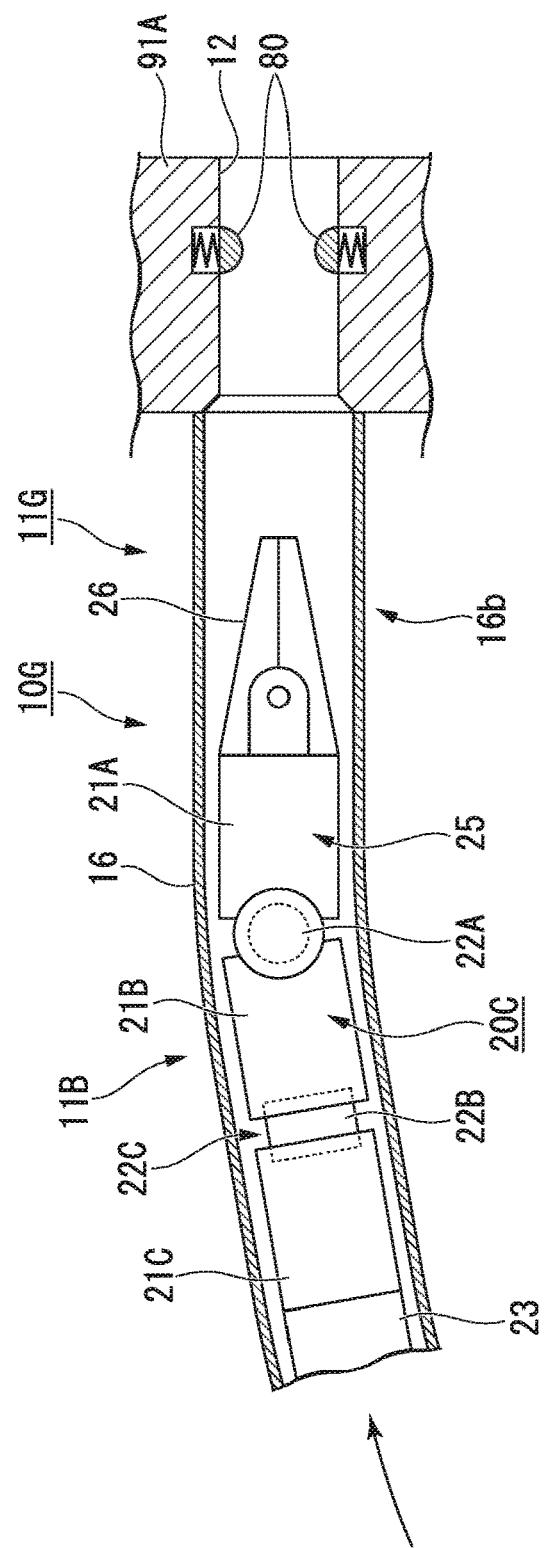
FIG. 19A is a schematic sectional view illustrating principal parts of a medical instrument used for the manipulator system initialization method of the fourth embodiment of the invention.
Figure 19B:
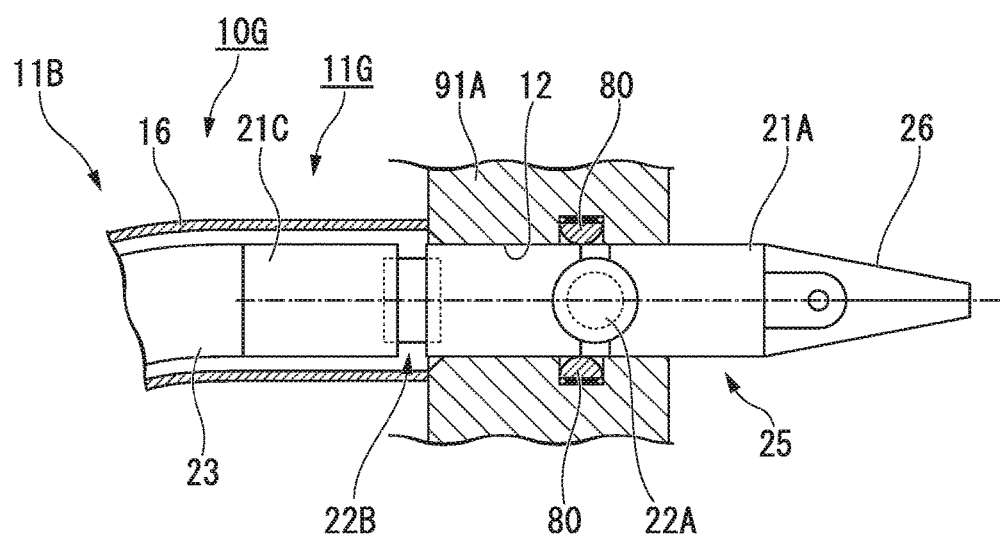
FIG. 19B is a schematic sectional view illustrating a shape defining member of the medical instrument used for the manipulator system initialization method of the fourth embodiment of the invention.
Figure 20:
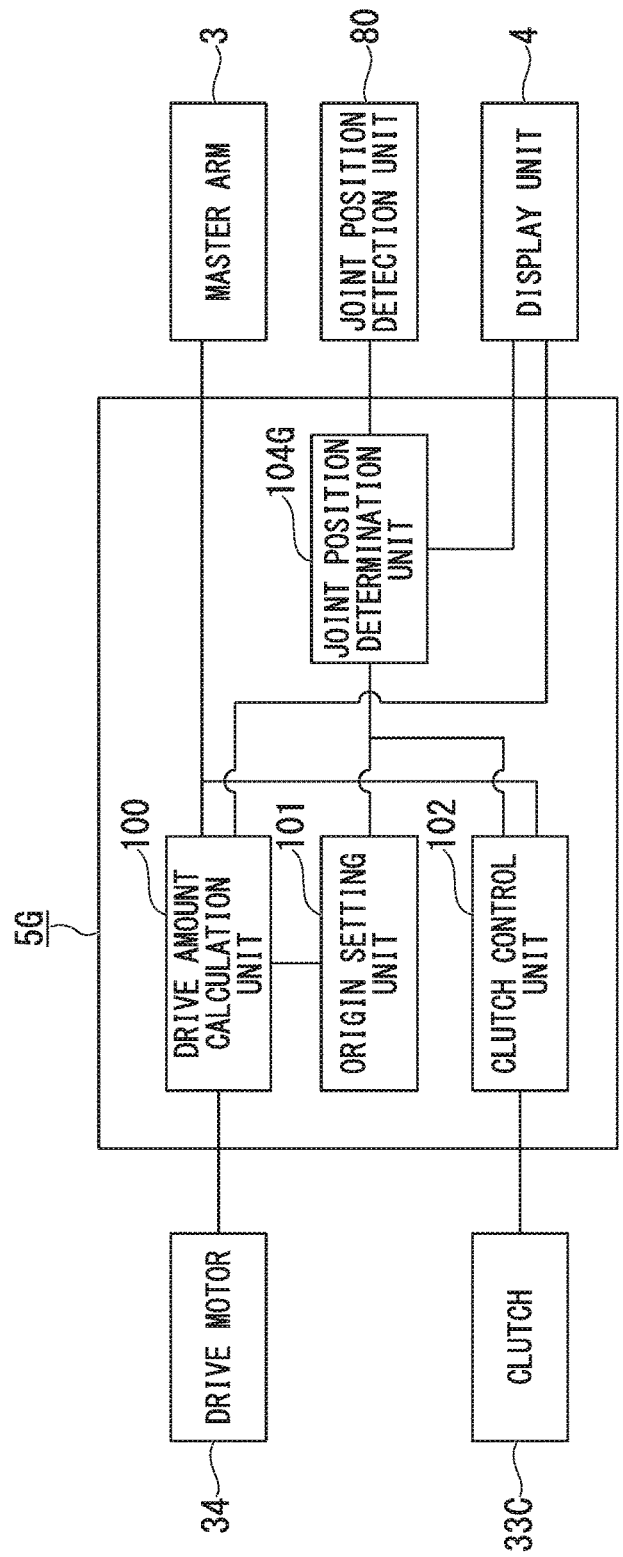
FIG. 20 is a functional block diagram of a control unit used for the manipulator system initialization method of the fourth embodiment of the invention.

FIG. 19A is a schematic sectional view illustrating principal parts of a medical instrument used for the manipulator system initialization method of the fourth embodiment of the invention. FIG. 19B is a schematic sectional view illustrating a shape defining member of the medical instrument used for the manipulator system initialization method of the fourth embodiment of the invention. FIG. 20 is a functional block diagram of a control unit used for the manipulator system initialization method of the fourth embodiment of the invention.

As illustrated in FIG. 1, a manipulator system 1G used for the manipulator system initialization method of the present embodiment includes an endoscope apparatus 10G for treatment and a control unit 5G (driving control unit), instead of the endoscope apparatus 10C for treatment and the control unit 5C of the manipulator system 1C in the above third embodiment.

The endoscope apparatus 10G for treatment includes an overtube 11G, instead of the overtube 11 of the endoscope apparatus 10C for treatment.

Hereinafter, differences from the aforementioned third embodiment will mainly be described.

As illustrated in FIGS. 19A and 19B, the overtube 11G has a distal end part 91A of which the length is shortened up to a length such that all of the joint parts 22 of the distal end bending part 25 cannot be inserted thereinto, instead of the distal end part 11A of the overtube 11.

In the present embodiment, as an example, the distal end part 91A has a length such that only one joint part 22 and portions of the pair of shaft-shaped parts 21 coupled to the joint part can be inserted thereinto.

The control unit 5CG, as illustrated in FIG. 20, includes a joint position determination unit 104G, instead of the joint position determination unit 104 of the control unit 5C of the above third embodiment.

The joint position determination unit 104G has a function to count the number of the distal ends of the shaft-shaped parts 21 that have reached the position of the joint position detection unit 80, and has a function to notify the origin setting unit 101 and the clutch control unit 102 of what number of a joint part 22 has succeeded in the setting of the joint angle, in addition to the function of the joint position determination unit 104. In the origin setting unit 101 and the clutch control unit 102, each operation is performed to the notified joint part 22.

For this reason, the joint position determination unit 104G also has the origin setting unit 101 and the clutch control unit 102 communicably connected thereto.

Next, the manipulator system initialization method using the medical instrument 20C of the present embodiment of the invention will be described.

Figure 21:
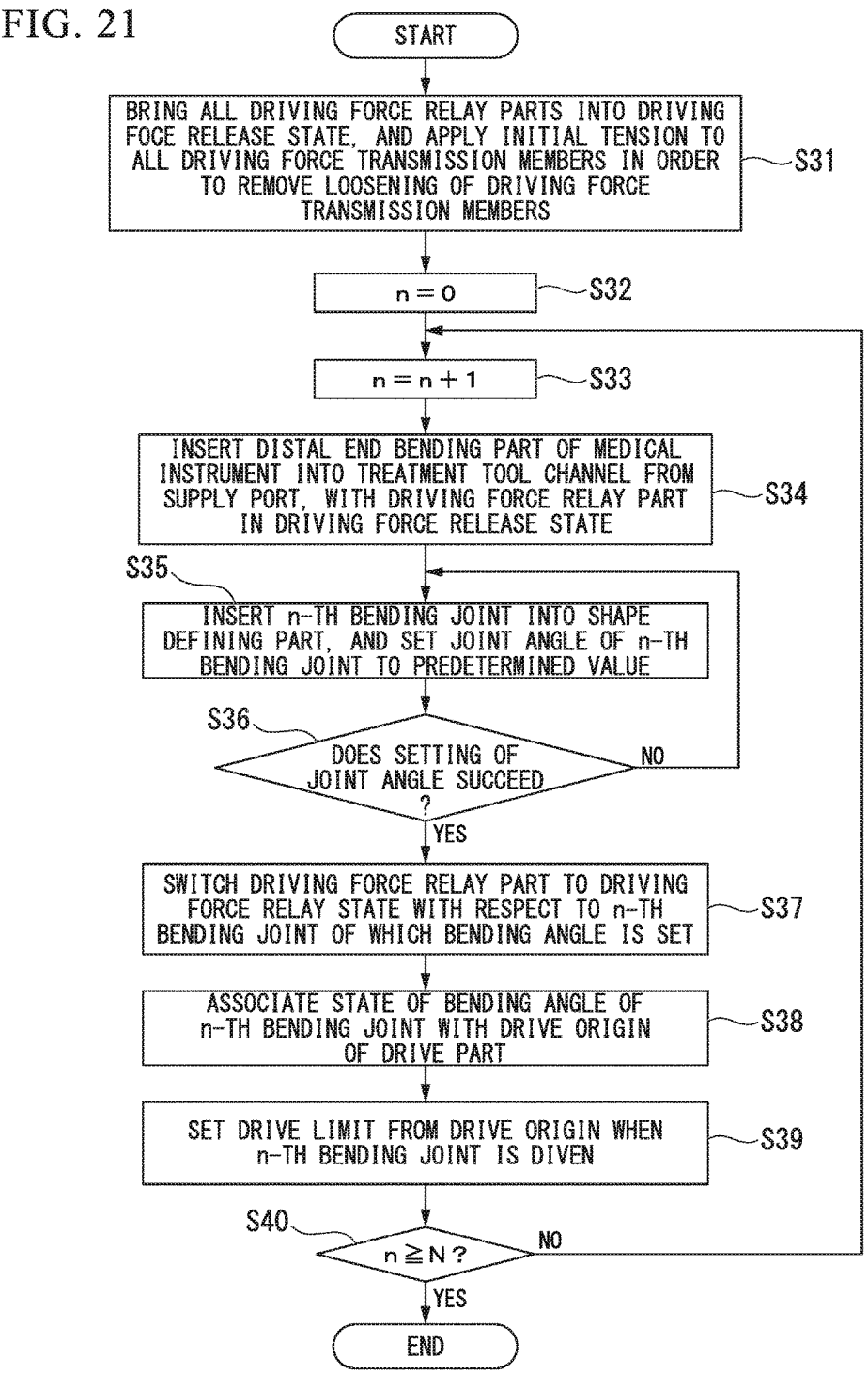
FIG. 21 is a flowchart illustrating the flow of the manipulator system initialization method of the fourth embodiment of the invention.

FIG. 21 is a flowchart illustrating the flow of the manipulator system initialization method of the fourth embodiment of the invention.

The manipulator system initialization method of the present embodiment is a method of executing Steps S31 to S40 illustrated in FIG. 21 according to the flow of FIG. 21.

Step S31 is the same step as Step S21 of the above third embodiment.

Next, Step S32 is performed. This step is a step of initializing a counter value n of the joint position determination unit 104G to 0.

Next, Step S33 is performed. This step is a step of updating the counter of the joint position determination unit 104G as n=n+1.

Steps S34 to S39 are almost the same steps as Steps S22 to S27 (refer to FIG. 17) in the above third embodiment except that these steps are performed using the overtube 11G and the joint position determination unit 104G notifies the origin setting unit 101 and the clutch control unit 102 of what number of the joint part 22 has succeeded in the joint angle.

That is, in the overtube 11G the joint position detection unit 80 detects the position of the distal end of each shaft-shaped part 21 on the proximal end side with respect to each joint part 22. Therefore, it is detected that the joint angle of the joint part 22 coupled to the distal end (distal end side) of this shaft-shaped part 21 has succeeded depending on this detection signal.

For example, in a case of n=1, the joint position detection unit 80 generates a detection signal in a case where the setting of the joint angle of the first joint part 22A from the distal end side in the distal end bending part 25 has succeeded.

Thus, in Steps S37 to S39, the origin setting unit 101 and the clutch control unit 102 perform the same operation as the above Steps S25 to S27 with respect to an n-th notified joint part 22.

Step S40 is a step of determining whether or not the counter value n has reached N or more that is the total number of the joint parts 22, in the joint position determination unit 104.

In a case where n is less than N, the processing proceeds to Step S33 where Steps S33 to S40 are repeated. That is, in Step S33, the counter value n is updated, and in Steps S34 to S36, the operator Op continues further insertion of the medical instrument 20C, and sets the joint angle of the next joint part 22 arranged on the proximal end side, in a similar way to the above.

The initialization operation is ended in a case where n is equal to or more than N. Accordingly, each joint part 22 of the medical instrument 20C is initialized.

According to the initialization method of the present embodiment, the axial length is short like the overtube 11G. Therefore, even in a case where the joint angles of all the joint parts 22 cannot be simultaneously set, the joint parts 22 can be initialized in order from the distal end side. Therefore, after the end of the initialization, a precise bending operation using the distal end bending part 25 can be performed similar to the above third embodiment.

According to the initialization method of the present embodiment, the length of the shape defining part 12 is the shortest, and just has to be a length such that only one joint part 22 and portions of a pair of shaft-shaped parts 21 coupled to the joint part can be inserted. For this reason, no matter how long the length of the distal end bending part 25 may be, the initialization operation is achieved in a slight space even in an inserted state into the body of the patient P like the overtube 11G.

In addition, in the description of the above respective embodiments and the above respective modification examples, an example in a case where the grasping part 26 that is grasping forceps is provided has been described as an end effector of a medical instrument. However, the end effector is not limited to the grasping part 26, and a suitable device configuration, for example, a high-frequency treatment tool, a local injection needle, peeling forceps, suction, and the like are possible according to the type of procedure. Additionally, the end effector is not limited to a movable mechanism like the grasping part 26, either. For example, an end effector of being only fixed to the distal end like the observation unit 15 of the endoscope apparatus 10 for treatment may be adopted.

In the description of the above respective embodiments and the above respective modification examples, examples in cases where the manipulator system initialization methods are initialization methods of medical manipulator systems have been described. However, the invention can also be similarly applied to manipulator systems other than the medical manipulator systems, for example, industrial manipulator systems. In this case, a medical instrument having the joint parts that rotate a rotating body can be replaced with instruments having joint parts that rotate a rotating body, industrial instruments, or industrial treatment tools.

In the description of the above respective embodiments and the above respective modification examples, an example in a case where the distal end bending part 25 has the two joint parts 22A and 22B the bending directions of which are different from each other has been described. However, the number and degree of freedom of joint parts can be appropriately set in consideration of the contents of a procedure, or the like. Additionally, the same mechanism as the bending part 11B in the overtube 11 may be used instead of the combination of the joint parts and the tubular parts. That is, in a case where a plurality of joint rings or bending pieces that are the shaft-shaped parts are coupled together by a turning joint that is the bending joint, it is possible to perform initialization in a similar way to the turning joint (including a case where a plurality of the turning joints are provided).

In the description of the above respective embodiments and the above respective modification examples, an example in a case where the distal end part 11A that forms the shape defining part 12 made of hard resin has been described. However, the distal end part 11A can also be made of a flexible material if the shape thereof is stable to such a degree that each joint part 22 in the driving force release state can be bent at a predetermined angle. That is, the distal end bending part 25 in the driving force release state is not particularly limited if a hard resin that keeps a fixed shape similar to the hard material is used.

Additionally, the shape defining part 12 may be constituted of a tubular member (a case where a plurality of the tubular members are provided) that is different from the distal end part 11A.

In the description of the above respective embodiments and the above respective modification examples, an example in a case where the predetermined value of the joint angle is a joint angle that brings the angle between the shaft-shaped parts 21 to be coupled together to 180° has been described. However, it is also possible to set a joint angle which brings the angle between the shaft-shaped parts 21 to be coupled together to an angle other than 180° to a predetermined value.

In this case, a bent tube shape can be adopted as the shape defining part 12.

In the description of the above respective embodiments and the above respective modification examples, an example in a case where the shape defining part consists of the shape defining part 12 having the hole shape has been described. However, it is not indispensable that the shape defining part have the hole shape.

If the shape defining part can define the joint angle of the bending joint, for example, a guide part with a groove shape that covers the outer periphery of the bending joint within a range equal to or more than a semiperimeter or a guide part with an appropriate shape that abuts against the outer peripheral surface of the bending joint at a plurality of positions and is positioned at a position where the joint angle reaches a predetermined value, besides the hole shape, can be adopted.

In the description of the above respective embodiments and the above respective modification examples, an example in a case where the drive limit is set only by the soft setting using the encoder of the drive motor 34 has been described. However, for example, as the drive motor 34, it is possible to adopt a drive part having a position sensor that can detect a position reaching an allowable limit of the rotational angle to perform the origin searching of the drive motor 34. As the position sensor, for example, sensors, such as an optical sensor and a mechanical sensor, can be adopted.

In this case, in the origin setting step, it is preferable to execute an origin searching step of performing searching for the drive part origin, on the basis of a detection output of the position sensor until the driving force relay part is switched to the driving force relay state.

In this step, for example, the origin searching such that the rotational angle of the drive part is changed to the center position of a position reaching the allowable limit by the position sensor is performed.

In this case, in a case where priority is given to the drive limit based on the position sensor, a substantial driving range can be prevented from being limited. Additionally, in a case where priority is given to the drive limit of the soft setting, the drive limit can be prevented from being set beyond the drive limit based on the position detecting sensor.

In the description of the above respective embodiments and the above respective modification examples, an example in a case where the operator Op manually inserts a medical instrument into the shape defining part 12 has been described. However, the medical instrument can be automatically inserted by including, for example, insertion mechanisms, such as a robot and an advancing and retracting mechanism.

In this case, if the joint position detection unit 80 is provided like the above second and third embodiments, it is possible to operate an insertion mechanism on the basis of this detection signal to automate the manipulator system initialization method of the invention.

In the description of the above third embodiment, an example in a case where the joint parts 22 are sequentially initialized one by one has been described. However, it is possible to appropriately set the length of the shape defining part 12 to simultaneously initialize two or more joint parts 22 to perform this initialization multiple times to initialize all the joint parts 22. In this case, the joint parts 22 initialized every time may be separate, or may be partially duplicate.

In the description of the above respective embodiments and the above respective modification examples, an example in a case where a medical instrument includes the distal end bending part 25 and the shape defining member consists of the distal end part 11A of the overtube 11 of the endoscope apparatus 10 for treatment has been described. In that case, both of the distal end bending part 25 of the medical instrument and the bending part 11B of the overtube 11 are electrically driven, so that the curved shape can be changed by the control unit.

However, the combination of the medical instrument and the shape defining member is not limited to this.

For example, the endoscope apparatus 10 for treatment can be replaced with a manual endoscope apparatus.

Additionally, instead of the endoscope apparatus 10 for treatment, a guide tube or a trocar can be adopted regardless of electric operation or manual operation. In this case, it is possible to use a hole provided in a portion of the guide tube or the trocar as the shape defining part. In this case, as the medical instrument, for example, an electric endoscope, such as the endoscope apparatus 10 for treatment, or a treatment tool having the joint parts at the distal end, such as the medical instrument 20, can be adopted.

In the description of the above respective embodiments and the above respective modification examples, an example in a case where a medical instrument is a flexible treatment tool has been described. However, the medical instrument can also be a hard treatment tool if the plurality of shaft-shaped parts coupled together by the bending joint are provided.

In the description of the above respective embodiments and the above respective modification examples, an example has been described in a case where a medical instrument includes the distal end bending part 25 and the shape defining member consists of the distal end part 11A inserted into the body of the patient P.

However, it is not indispensable that the shape defining member be inserted into the body of the patient P. For example, a tubular calibration tool provided outside the body of the patient P can be adopted as the shape defining member.

That is, as the manipulator system initialization method of the invention, a method of preparing the shape defining member as a jig other than a manipulator, and performing initialization outside the body of the patient P is possible.

All the constituent elements described in the above may be carried out by appropriate combination or elimination in the scope of the technical idea of the invention.

For example, it is possible to perform the manipulator system initialization method of the above fourth embodiment using the distal end part 11A of the endoscope apparatus 10C for treatment of the above third embodiment.

In this case, since all the joint parts 22 are inserted into the shape defining part 12, the joint parts are sequentially initialized from the distal end side even if the setting of the joint angle is possible.

Additionally, in the above third embodiment, the position of the joint position detection unit 80 is arranged closer to the proximal end side. Thus, even if the distal end part 11A is provided, it is also possible to perform the same initialization operation as that of the above fourth embodiment.

What is claimed is:

1. A method for initializing a manipulator system, the manipulator system including a bending joint and a plurality of shaft-shaped parts coupled together by the bending joint, a wire configured to transmit a driving force to the bending joint to bend the bending joint, a motor configured to supply the driving force to the wire, and a clutch configured to switch between a driving force relay state where the clutch relays the driving force supplied by the motor to the wire and a driving force release state where the clutch does not relay the driving force supplied by the motor to the wire so that the bending joint moves freely, the method comprising:

controlling the clutch to be in the driving force release state while the bending joint and the plurality of shaft-shaped parts are inserted into a shape defining part opening defined by an overtube to thereby bring a joint angle of the bending joint to a predetermined value;

controlling the clutch to switch to the driving force relay state with respect to the bending joint having the joint angle at the predetermined value; and associating the joint angle of the bending joint brought to the predetermined value with a drive origin of the motor.

2. The method according to claim 1, comprising:

generating a driving command value to drive the motor to supply the driving force that is transmitted by the wire to bend the bending joint, wherein the driving command value is generated to not exceed a drive limit, wherein the drive limit corresponds to a predetermined amount of driving of the motor from the drive origin.

3. The method according to claim 1, wherein the manipulator system includes a position sensor configured to detect a position of the motor, and wherein the method comprises:

determining the drive origin of the motor based on the position of the motor detected by the position sensor.

4. The method according to claim 1, wherein controlling the clutch to be in the driving force relay state comprises controlling the clutch to couple the motor to the wire, and wherein controlling the clutch to be in the driving force release state comprises controlling the clutch to decouple the motor from the wire.

5. The method according to claim 1, comprising:

prior to associating the joint angle of the bending joint brought to the predetermined value with the drive origin of the motor, applying an initial tension to the wire in order to remove loosening of the wire.

6. The method according to claim 1, comprising:

determining whether the joint angle of the bending joint has been brought to the predetermined value by detecting an insertion state where the bending joint and the shaft-shaped parts are inserted into the shape defining part opening defined by the overtube.

7. The method according to claim 1, wherein the manipulator system comprises a plurality of the bending joint and a plurality of the drive parts respectively coupled together by the plurality of the bending joint, and wherein the method comprises:

controlling the clutch to be in the driving force release state while the plurality of the bending joint and the plurality of shaft-shaped parts are inserted into the shape defining part opening defined by the overtube to thereby bring the joint angle of each of the plurality of the bending joint to the predetermined value;

controlling the clutch to switch to the driving force relay state with respect to the plurality of the bending joint having the joint angle at the predetermined value; and associating the each of the joint angle of the plurality of the bending joint brought to the predetermined value with the drive origin of the motor.

8. A manipulator system comprising:
a bending joint and a plurality of shaft-shaped parts coupled together by the bending joint;
a wire configured to transmit a driving force to the bending joint to bend the bending joint;
a motor configured to supply the driving force to the wire;
a clutch configured to switch between a driving force relay state where the clutch relays the driving force supplied by the motor to the wire and a driving force release state where the clutch does not relay the driving force supplied by the motor to the wire so that the bending joint moves freely; and
a processor comprising hardware, wherein the processor is configured to:
control the clutch to be in the driving force release state while the bending joint and the plurality of shaft-shaped parts are inserted into a shape defining part opening defined by an overtube to thereby bring a joint angle of the bending joint to a predetermined value;
control the clutch to switch to the driving force relay state with respect to the bending joint having the joint angle at the predetermined value; and
associate the joint angle of the bending joint brought to the predetermined value with a drive origin of the motor.

9. The manipulator system according to claim 8, wherein in the driving force relay state, the clutch is configured to couple the motor to the wire, and
wherein in the driving force release state, the clutch is configured to decouple the motor from the wire.

10. The manipulator system according to claim 8, wherein the processor is configured to:
generate a driving command value to drive the motor to supply the driving force that is transmitted by the wire to bend the bending joint,
wherein the driving command value is generated to not exceed a drive limit, wherein the drive limit corresponds to a predetermined amount of driving of the bending joint from the drive origin.

11. The manipulator system according to claim 8, further comprising:
a position sensor configured to detect a position of the motor,
wherein the processor is configured to determine the drive origin of the motor based on the position of the motor detected by the position sensor.

12. A non-transitory computer-readable storage medium storing instructions for initializing a manipulator system, the manipulator system including a bending joint and a plurality of shaft-shaped parts coupled together by the bending joint, a wire configured to transmit a driving force to the bending joint to bend the bending joint, a motor configured to supply the driving force to the wire, and a clutch configured to switch between a driving force relay state where the clutch relays the driving force supplied by the motor to the wire and a driving force release state where the clutch does not relay the driving force supplied by the motor to the wire so that the bending joint moves freely, the instructions causing the computer to at least:
control the clutch to be in the driving force release state while the bending joint and the plurality of shaft-shaped parts are inserted into a shape defining part opening defined by an overtube to thereby bring a joint angle of the bending joint to a predetermined value;
control the clutch to switch to the driving force relay state with respect to the bending joint having the joint angle at the predetermined value; and
associate the joint angle of the bending joint brought to the predetermined value with a drive origin of the motor.

13. The non-transitory computer-readable storage medium according to claim 12, wherein the instructions cause the computer to: generate a driving command value to drive the motor to supply the driving force that is transmitted by the wire to bend the bending joint, wherein the driving command value is generated to not exceed a drive limit, wherein the drive limit corresponds to a predetermined amount of driving of the motor from the drive origin.

* * * * *